US012767649B2

(12) United States Patent
Jean-Baptiste-Dit-Dominique et al.

(10) Patent No.: US 12,767,649 B2
(45) Date of Patent: Oct. 20, 2026

(54) PROCESS FOR THE SYNTHESIS OF 5-((2-METHYL-1H-IMIDAZOL-1-YL)METHYL)FURAN-2-CARBALDEHYDE AND OF NITRONES FROM 5-((2-METHYL-1H-IMIDAZOL-1-YL) METHYL)FURAN-2-CARBALDEHYDE

(71) Applicant: COMPAGNIE GENERALE DES ETABLISSEMENTS MICHELIN, Clermont-Ferrand (FR)

(72) Inventors: Francois Jean-Baptiste-Dit-Dominique, Clermont-Ferrand (FR); Marc Sutter, Clermont-Ferrand (FR); Sergey Ivanov, Clermont-Ferrand (FR); Robert Ngo, Clermont-Ferrand (FR); Luana Marty, Clermont-Ferrand (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 286 days.

(21) Appl. No.: 18/722,322

(22) PCT Filed: Dec. 19, 2022

(86) PCT No.: PCT/FR2022/052416
§ 371 (c)(1),
(2) Date: Jun. 20, 2024

(87) PCT Pub. No.: WO2023/118715
PCT Pub. Date: Jun. 29, 2023

(65) Prior Publication Data
US 2025/0084070 A1 Mar. 13, 2025

(30) Foreign Application Priority Data
Dec. 21, 2021 (FR) ....................................... 2114133

(51) Int. Cl.
*C07D 405/06* (2006.01)

(52) U.S. Cl.
CPC .................................. *C07D 405/06* (2013.01)

(58) Field of Classification Search
CPC .................................................... C07D 405/06
See application file for complete search history.

(56) References Cited

U.S. PATENT DOCUMENTS

| | | | |
|---|---|---|---|
| 4,729,851 | A | 3/1988 | Braunling et al. |
| 10,202,471 | B2 | 2/2019 | Ugolnikov et al. |
| 11,034,780 | B2 | 6/2021 | Ugolnikov et al. |
| 2003/0212185 | A1 | 11/2003 | Vasseur |
| 2016/0251456 | A1 | 9/2016 | Ugolnikov et al. |
| 2019/0119412 | A1 | 4/2019 | Ugolnikov et al. |
| 2022/0235164 | A1 | 7/2022 | Dit Dominique |

FOREIGN PATENT DOCUMENTS

| | | | |
|---|---|---|---|
| WO | 02/10269 | A2 | 2/2002 |
| WO | 2015/059269 | A1 | 4/2015 |
| WO | 2020/249623 | A1 | 12/2020 |
| WO | 2020/249631 | A1 | 12/2020 |

OTHER PUBLICATIONS

International Search Report dated Apr. 25, 2023, in corresponding PCT/FR2022/052416 (5 pages).
H. Quiroz-Florentino, et al., "Total Synthesis of Naturally Occurring Furan Compounds 5-{[(4-Hydroxybenzyl)oxy] methyl}-2-furaldehyde and Pichiafuran C", Synthesis 2011, No. 7, pp. 1106-1112.
M. Brasholz, et al., "Highly efficient dehydration of carbohydrates to 5-(chloromethyl)furfural (CMF), 5-(hydroxymethyl) furfural (HMF) and levulinic acid by biphasic continuous flow processing", Green Chem., 2011, 13, 1114.
N. Kumari, et al., "Synthesis of 5-Bromomethylfurfural from Cellulose as a Potential Intermediate for Biofuel", Eur. J. Org. Chem. 2011, 1266-1270.
D.R. Lane, et al., "Experimental studies towards optimization of the production of 5-(chloromethyl)furfural (CMF) from glucose in a two-phase reactor", Renewable Energy 85 (2016) 994-1001.
M. Mascal, "5-(Chloromethyl) furfural (CMF): A Platform for Transforming Cellulose into Commercial Products", ACS Sustainable Chem. Eng. 2019, 7, 5588-5601.
M. Mascal, et al., "Direct, High-Yield Conversion of Cellulose into Biofuel", Angew. Chem. Int. Ed. 2008, 47, 7924-7926.
O. Kamm, "Working with Hazardous Chemicals", Organic Syntheses, Coll. vol. 1, p. 445 (1941); vol. 4, p. 57 (1925).
(Continued)

*Primary Examiner* — Shawquia Jackson
(74) *Attorney, Agent, or Firm* — VENABLE LLP

(57) ABSTRACT

A process for synthesizing 5-((2-methyl-1H-imidazol-1-yl) methyl)furan-2-carbaldehyde from a mixture comprising a carbohydrate, an alkali or alkaline-earth metal chloride, hydrochloric acid, water, an organic solvent, namely a water-insoluble polar aprotic solvent, and optionally a phase-transfer agent, proceeds via the formation of 5-(chloromethyl)furan-2-carbaldehyde, without isolating this synthesis intermediate. A process also synthesizes a compound of formula (III) below:

(III)

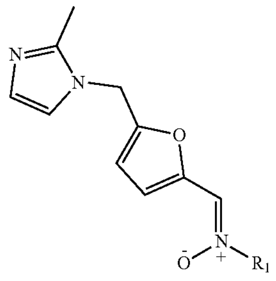

from 5-((2-methyl-1H-imidazol-1-yl)methyl)furan-2-carbaldehyde.

19 Claims, 1 Drawing Sheet

(56) References Cited

OTHER PUBLICATIONS

K. Sanda, et al., "Synthese Du 5-Bromomethyl-Et Du. 5-Chloromethyl-2-Furannecarboxaldehyde", Carbohydrate Research, 187 (1989) 15-23 with English abstract.
J.R. Bernardo, et al., "HReO4 as highly efficient and selective catalyst for the conversion of carbohydrates into value added chemicals", Molecular Catalysis 465 (2019) 87-94.

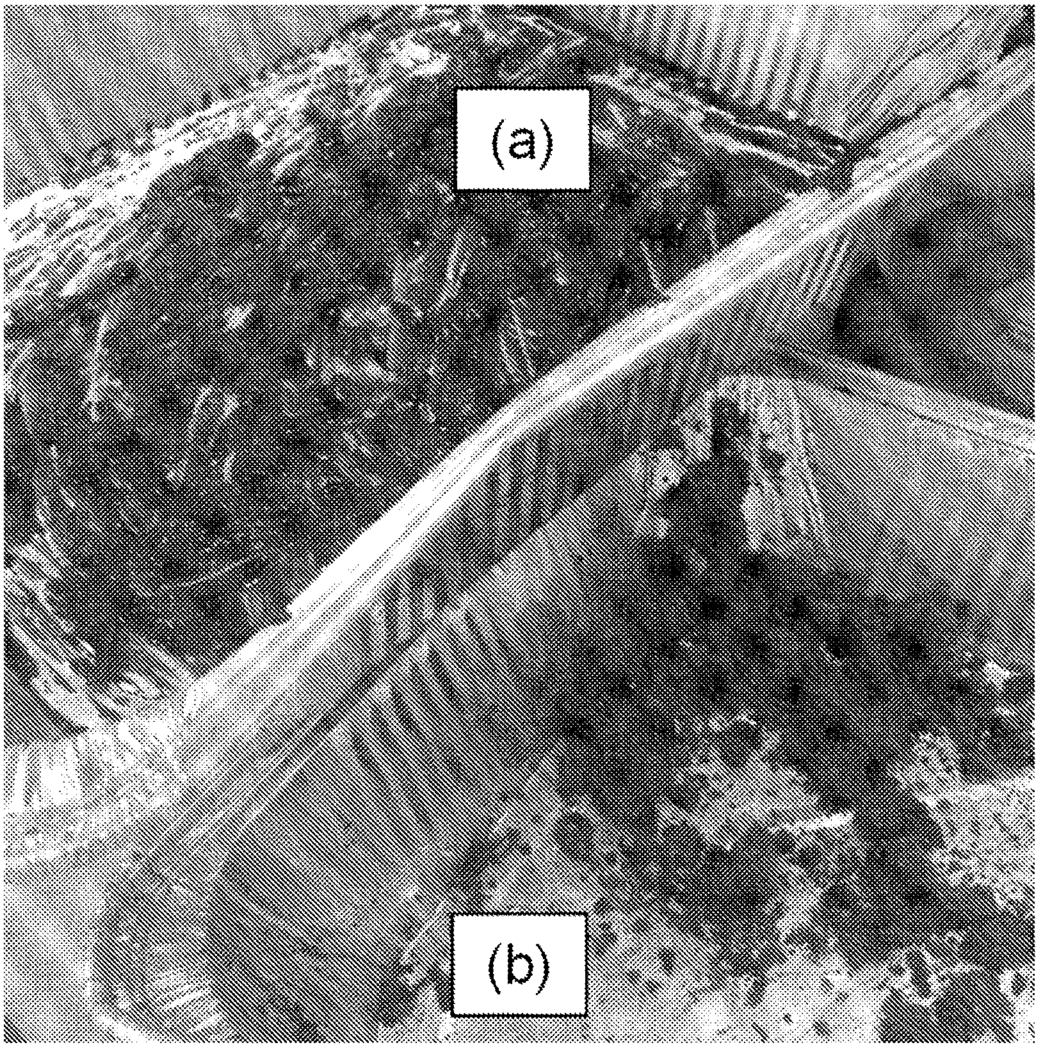
(a)
(b)

PROCESS FOR THE SYNTHESIS OF 5-((2-METHYL-1H-IMIDAZOL-1-YL)METHYL) FURAN-2-CARBALDEHYDE AND OF NITRONES FROM 5-((2-METHYL-1H-IMIDAZOL-1-YL)METHYL) FURAN-2-CARBALDEHYDE

TECHNICAL FIELD OF THE INVENTION

The present invention relates to a process for synthesizing 5-((2-methyl-1H-imidazol-1-yl)methyl)furan-2-carbaldehyde (compound of formula Chem. I below, also referred to as compound of formula (I)), and also a process for synthesizing a nitrone of formula Chem. III (also referred to as nitrone or compound of formula (III)), via the synthesis of 5-((2-methyl-1H-imidazol-1-yl)methyl)furan-2-carbaldehyde according to the invention.

or may not be aromatic and B is an imidazole ring. When an elastomer grafted with this compound is mixed with reinforcing fillers in a rubber composition, the compromise between stiffness in the cured state and hysteresis of this rubber composition is improved relative to rubber compositions not comprising a grafted elastomer. These compounds are thus particularly advantageous.

More recently, it has been discovered that a family of particular 1,3-dipolar compounds comprising a heteroaromatic ring and an imidazole ring (WO 2020/249631 and WO 2020/249623) exhibits an improved grafting yield compared to the 1,3-dipolar compounds of WO 2015/059269 comprising an aromatic or non-aromatic ring and an imidazole ring.

WO 2020/249623 thus describes the synthesis of 1-(5-((2-methyl-1H-imidazol-1-yl)methyl)furan-2-yl)-N-phenylmethanimine oxide according to the the following reaction scheme Chem. SR1:

[Chem. SR1]

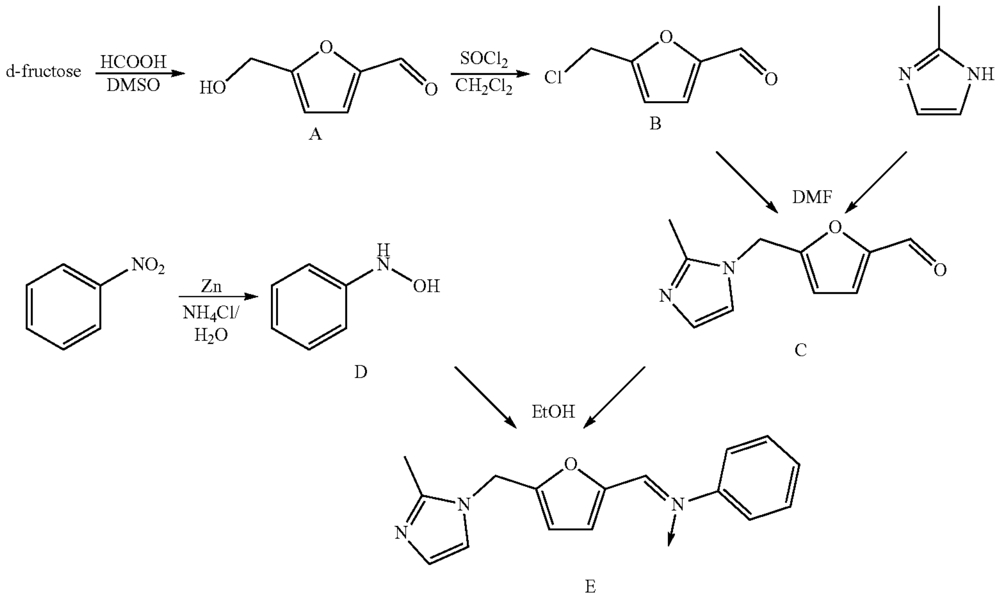

The nitrones of formula (III), in particular the 1-(5-((2-methyl-1H-imidazol-1-yl)methyl)furan-2-yl)-N-phenylmethanimine oxide of formula (IIIa), obtained according to the process of the invention are used as modifying agent intended to functionalize unsaturated polymers along the polymer chain.

PRIOR ART

Modification of the chemical structure of a polymer, such as the functionalization thereof by grafting, is particularly sought when it is desired to bring together a polymer and a filler in a composition. This modification generally has an impact on the chemical and physical properties of the polymer, and also on the properties of the compositions containing it.

Consequently, it is still a concern to be able to have novel functional polymers which make it possible to improve the reinforcement of a polymer composition comprising a reinforcing filler.

WO 2015/059269 describes compounds of formula Q-A-B in which the group Q comprises a dipole containing at least one nitrogen atom, A is a divalent group which may This synthesis process thus comprises 5 steps.

- synthesis and isolation of 5-(hydroxymethyl)furan-2-carbaldehyde (product A) from D-fructose in DMSO;
- synthesis and isolation of 5-(chloromethyl)furan-2-carbaldehyde (product B) from product A in dichloromethane;
- synthesis and isolation of 5-((2-methyl-1H-imidazol-1-yl)methyl)furan-2-carbaldehyde (product C) by reaction of product B and 2-methylimidazole in DMF;
- synthesis and isolation of N-phenylhydroxylamine (product D) from nitrobenzene; and
- synthesis and isolation of 1-(5-((2-methyl-1H-imidazol-1-yl)methyl)furan-2-yl)-N-phenylmethanimine oxide (product E) from product D in ethanol.

Data from the literature (Green Chem., 2011, 13, 1114-1117; Eur. J. Org. Chem. 2011, 1266-1270; Renewable Energy. 2016, 85, 994-1001; ACS Sustainable Chem. Eng., 2019, 7, 5588-5601; and Angew. Chem, Int. Ed., 2008, 47, 7924-7926) also describe the synthesis of product B from glucose, fructose or else cellulose in an acid medium without it being necessary to isolate product A. A variant of the process according to WO 2020/249623 can therefore comprise 4 steps with isolation of each of the reaction intermediates B, C and D in the above reaction scheme.

The process for preparing the compounds from WO 2020/249623, in particular of the 1-(5-((2-methyl-1H-imidazol-1-yl)methyl)furan-2-yl)-N-phenylmethanimine oxide, is complex (multistep synthesis) and requires procedures for isolating the intermediate products. Specifically, for each reaction intermediate, steps of purifying by filtration, of isolating by removal of the synthesis solvents, and then of redissolving for the step of preparing the next intermediate are necessary and lead to the potential loss of material (low overall yield), to the increase of the individual steps, of the overall cycle time, of the overall energy consumption and of the overall amount of solvent used. In addition, several different solvents are often used, such as polar solvents (dichloromethane (DCM), dimethylformamide (DMF), methyl tert-butyl ether (MTBE), ethanol), aliphatic alkanes (petroleum ether) or aromatic alkanes (toluene), to facilitate the reaction, the isolation by washing/extraction and/or filtration steps, then the drying of the intermediate products. However, managing a multiplicity of solvents complicates the synthesis process. Moreover, this multiplicity of solvents also imparts health, safety and environmental (HSE) constraints due, for example, to the toxicity of certain solvents (DMF for example has a toxicological profile which limits its use) or to their volatile and flammable nature (MTBE for example has a flash point of −33° C.). Constraints in terms of waste and effluent management should also be noted, particularly with toxic effluents, which may require expensive investments. Finally, toxic solvent residues (>0.3% by weight) can lead to the final product being classified as a toxic solvent.

It is still a concern to be able to have novel processes for obtaining these dipolar compounds bearing an imidazole function, which make it possible to reduce the number of synthesis intermediate isolation steps, to reduce the cycle times, to reduce the amount of solvents used, reducing the number of different solvents used, to increase productivity by concentrating the medium, to limit the use of toxic or flammable solvents, to increase yields by limiting the formation of by-products and ultimately to reduce the cost of producing these additives.

SUMMARY OF THE INVENTION

The applicant has thus developed a novel process for synthesizing a 1,3-dipolar compound comprising a heteroaromatic ring and an imidazole ring, namely the nitrones of formula (III), in particular the 1-(5-((2-methyl-1H-imidazol-1-yl)methyl)furan-2-yl)-N-phenylmethanimine oxide of formula (IIIa), which makes it possible to overcome the drawbacks listed above.

The invention relates to a process for the preparation of a compound of formula Chem. I:

[Chem. I]

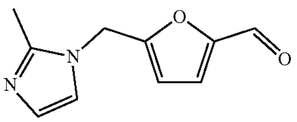

comprising the following successive steps:

(i) preparing a mixture comprising a carbohydrate, an alkali or alkaline-earth metal chloride, hydrochloric acid, water, an organic solvent and optionally a phase-transfer agent, said mixture being heated to a temperature within a range of from 35° C. to 90° C., preferentially within a range of from 45° C. to 80° C., particularly preferably within a range of from 55° C. to 75° C., said organic solvent being a water-insoluble polar aprotic solvent, and said carbohydrate being a monosaccharide, a polysaccharide or a mixture thereof, (ii) cooling the mixture obtained from step (i) to give a cooled mixture, separating the cooled mixture into an aqueous phase and an organic phase, and recovering the organic phase, said organic phase comprising the organic solvent and a compound of formula Chem. II:

[Chem. II]

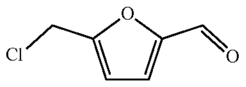

(iii) mixing 2-methylimidazole and the organic phase obtained from step (ii), the 2-methylimidazole being in molar excess relative to the compound of formula Chem. II;

(iv) recovering the compound of formula Chem. I formed following step (iii).

Preferentially, the carbohydrate is a monosaccharide, preferably fructose such as D-fructose.

Preferentially, the organic solvent is toluene.

Preferentially, during step (i) of the process, the amount of hydrochloric acid is within a range of from 3 to 7 molar equivalents, preferentially from 3.5 to 6 molar equivalents, particularly preferably from 4 to 5 molar equivalents relative to the amount of monosaccharide units present in the carbohydrate.

Preferentially, during step (i) of the process, the amount of chloride ions supplied by the alkali or alkaline-earth metal chloride is within a range of from 1.2 to 2.6 molar equivalents, preferentially within a range of from 1.6 to 2.4 molar equivalents, particularly preferably within a range of from 1.7 to 2.2 molar equivalents relative to the amount of monosaccharide units present in the carbohydrate.

Preferentially, the alkali metal or alkaline-earth metal chloride is chosen from magnesium chloride and lithium chloride, and is preferentially magnesium chloride.

Preferentially, the phase-transfer agent is a quaternary ammonium halide, for example a tetra($C_1$-$C_{20}$ alkyl)ammonium halide (e.g. bromide), preferentially hexadecyltrimethylammonium bromide, the amount of which is advantageously within a range of from 0.001 to 0.01 molar equivalents relative to the amount of monosaccharide units present in the carbohydrate.

Preferentially, step (i) comprises the following steps:

(i1) preparing a composition comprising the carbohydrate, the alkali or alkaline-earth metal chloride, the hydrochloric acid, the water, and optionally the phase-transfer agent; and (i2) adding, preferably in semi-continuous mode, the composition obtained from step (i1) to the organic solvent heated to a temperature within a range of from 35° C. to 90° C., in particular from 45° C. to 80° C., preferentially from 55° C. to 75° C.;

or comprises the following steps:

(i1) adding the carbohydrate to the organic solvent heated to a temperature within a range of from 35° C. to 90° C., in particular from 45° C. to 80° C., preferentially from 55° C. to 75° C.;

(i2) preparing a composition comprising the alkali or alkaline-earth metal chloride, the hydrochloric acid, the water, and optionally the phase-transfer agent; and (i3) adding, preferably in semi-continuous mode, the composition obtained from step (i2) to the heated organic solvent comprising the carbohydrate obtained from step (i1);

or comprises the following steps:

(i1) preparing a composition comprising the carbohydrate and the water;

(i2) preparing a composition comprising the organic solvent, the hydrochloric acid, the alkali or alkaline-earth metal chloride, and optionally the phase-transfer agent, said composition being heated to a temperature within a range of from 35° C. to 90° C., in particular from 45° C. to 80° C., preferentially within a range of from 55° C. to 75° C.; and (i3) adding, preferably in semi-continuous mode, the composition obtained from step (i1) to the heated composition obtained from step (i2);

or comprises the following steps:

(i1) preparing a composition comprising the organic solvent, the hydrochloric acid, the alkali or alkaline-earth metal chloride, the water and optionally the phase-transfer agent, said composition being heated to a temperature within a range of from 35° C. to 90° C., in particular from 45° C. to 80° C., preferentially from 55° C. to 75° C.; and (i2) adding the carbohydrate to the heated composition obtained from step (i1);

or comprises the following steps:

(i1) preparing a composition comprising the carbohydrate, the organic solvent, the alkali or alkaline-earth metal chloride, and optionally the phase-transfer agent, said composition being heated to a temperature within a range of from 35° C. to 90° C., in particular from 45° C. to 80° C., preferentially from 55° C. to 75° C.; and (i2) adding, preferably in semi-continuous mode, a solution of hydrochloric acid to the heated composition obtained from step (i1).

Preferentially, step (ii) comprises, after the cooling step and before the separation step, a step of filtering the cooled mixture in order to remove the solid materials present, preferably with a step of washing the solid materials with organic solvent, preferably with the organic solvent from step (i).

Preferentially, the amount of 2-methylimidazole during step (iii) is within a range of from 2.0 to 3.0, in particular from 2.0 to 2.5, preferably from 2.1 to 2.2 molar equivalents relative to the amount of the compound of formula Chem. II.

Preferentially, the mixture obtained during step (iii) comprising the 2-methylimidazole and the organic phase obtained from step (ii) is maintained at a temperature within a range of from 50° C. to 90° C., more preferentially 60° C. to 80° C., preferably from 65° C. to 75° C., preferentially for a period of time within a range of from 2 to 8 hours, preferably from 3 to 6 hours.

Preferentially, step (iii) comprises the following steps:

(iii1) adding, preferably in semi-continuous mode, at room temperature, a fraction of the organic phase obtained from step (ii) to the 2-methylimidazole;

(iii2) heating the composition obtained from step (iii1) to a temperature within a range of from 50° C. to 90° C., preferably from 60° C. to 80° C., more preferentially from 65° C. to 75° C.; and (iii3) adding, preferably in semi-continuous mode, the remaining fraction of the organic phase obtained from step (ii) to the heated composition obtained from step (iii2);

or comprises the following step:

(iii1) adding, preferably in semi-continuous mode, the 2-methylimidazole to the organic phase obtained from step (ii) heated to a temperature within a range of from 50° C. to 90° C., preferably from 60° C. to 80° C., more preferentially from 65° C. to 75° C.

The invention also relates to a process for the preparation of a compound of formula Chem. III:

[Chem. III]

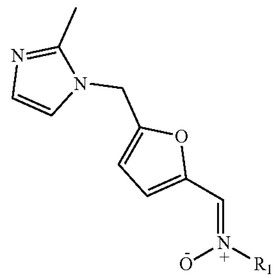

comprising the following steps:

(a) preparing a compound of formula Chem. I by a process according to the invention as described above;

(b) reacting the compound of formula Chem. I obtained in step (a) with a compound of formula $R_1$—$NO_2$ in the presence of a reducing agent, preferentially zinc, in order to form the compound of formula Chem. III; and (c) recovering the compound of formula Chem. III, wherein $R_1$ is selected from the group consisting of linear or branched $C_1$-$C_{20}$ alkyls; $C_3$-$C_{20}$ cycloalkyls optionally substituted with one or more preferably saturated, linear or branched aliphatic hydrocarbon chains; and $C_6$-$C_{20}$ aryls optionally substituted with one or more preferably saturated, linear or branched aliphatic hydrocarbon chains; preferably $R_1$ is a $C_6$-$C_{20}$ aryl optionally substituted with one or more $C_1$-$C_6$ alkyls, preferably one or more $C_1$-$C_3$ alkyls; more preferentially still $R_1$ is a $C_6$ aryl optionally substituted with one or more $C_1$-$C_6$ alkyls, preferably one or more $C_1$-$C_3$ alkyls.

Preferentially, step (b) comprises the following steps:

(b1) preparing a composition comprising the compound of formula Chem. I obtained in step (a), an ammonium salt such as ammonium chloride and a water/ethanol mixture, advantageously with a water/ethanol ratio as percentage by weight within a range of from 1/99 to 50/50, preferentially within a range of from 5/95 to 30/70, particularly preferably in a range of from 7/93 to 15/85;

(b2) adding the compound $R_1$—$NO_2$ to the composition obtained in step (b1), preferentially in an amount within a range of from 0.80 to 1.20 molar equivalents, preferentially from 0.90 to 1.10 molar equivalents, particularly preferably from 0.95 to 1.05 molar equivalents relative to the amount of the compound of formula Chem. I; and (b3) adding, preferably in semi-continuous mode, zinc to the composition obtained in step (b2) maintained at a temperature in a range of from 15° C. to 25° C., preferentially from 15° C. to 22° C., during the addition step.

Preferentially, the composition resulting from step (b3) is maintained at a temperature in a range of from 15° C. to 25° C., preferentially from 15° C. to 22° C., for a period of time within a range of from 4 to 6 hours.

The process according to the invention thus makes it possible to reduce the number of chemical steps compared to the prior art, while using solvents that are more acceptable from a toxicity standpoint.

The steps of the process for synthesizing the nitrones of formula (III) according to the invention are depicted in the reaction scheme Chem. SR2 below from a carbohydrate, D-fructose being preferred:

phase/aqueous phase two-phase medium during the synthesis of the compound of formula (II) limits the generation of decomposition by-products in the reaction medium.

Moreover, the preparation of the compound of formula (II) in situ in the process according to the invention makes it possible, unexpectedly, to synthesize the compound of formula (I) with yields greater than those obtained from a commercial compound of formula (II).

As detailed in the description of the invention, the process according to the invention can be carried out using carbohydrates other than fructose, for instance a polysaccharide such as cellulose or a monosaccharide such as glucose.

[Chem. SR2]

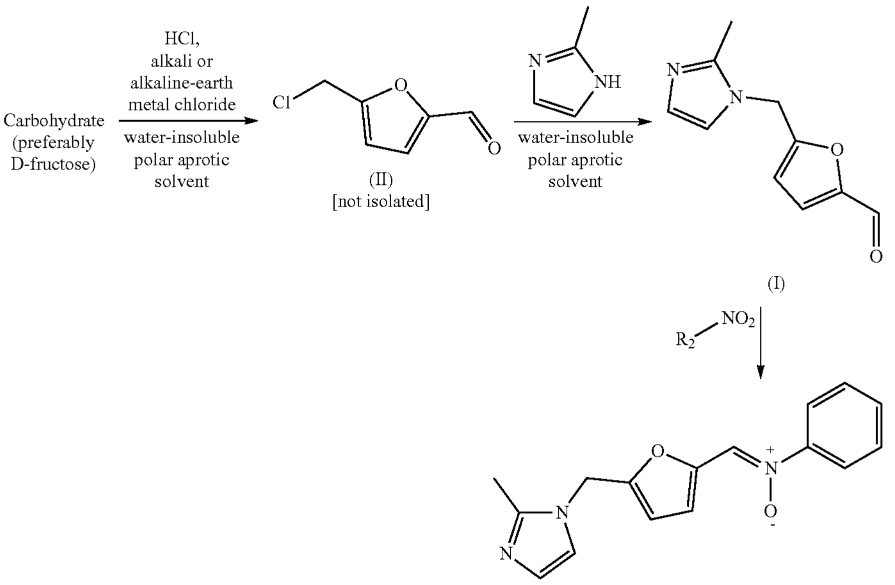

(II) [not isolated]

(I)

(IIIb)

wherein $R_1$ is selected from the group consisting of linear or branched $C_1$-$C_{20}$ alkyls $C_3$-$C_{20}$ cycloalkyls optionally substituted with one or more preferably saturated, linear or branched aliphatic hydrocarbon chains; and $C_6$-$C_{20}$ aryls optionally substituted with one or more preferably saturated, linear or branched aliphatic hydrocarbon chains.

5-(Chloromethyl)furan-2-carbaldehyde, named product B in the synthesis process from the prior art WO 2020/249623, is the compound of formula Chem. II or (II) in the preparation process according to the invention.

5-((2-Methyl-1H-imidazol-1-yl)methyl)furan-2-carbaldehyde, named product C in the synthesis process from the prior art WO 2020/249623, is the compound of formula Chem. I or (I) according to the invention.

1-(5-((2-Methyl-1H-imidazol-1-yl)methyl)furan-2-yl)-N-phenylmethanimine oxide, named product E in the synthesis process from the prior art WO 2020/249623, is the compound of formula Chem. IIIa or (IIIa) in the preparation process according to the invention, namely the compound of formula (III) with $R_1$=phenyl.

According to the process of the invention, the number of individual steps is thus reduced to 2 with isolation of only the compounds 5-((2-methyl-1H-imidazol-1-yl)methyl) furan-2-carbaldehyde (compound of formula (I)) and the nitrone of formula (III), using more acceptable solvents with optimized synthesis yields. In addition, the use of an organic When the carbohydrate is a polysaccharide, it will be hydrolyzed beforehand in the acid medium to give monosaccharide during step (i).

The monosaccharide is then converted into a compound of formula (II) during step (i) of the process according to the invention.

DESCRIPTION OF THE FIGURES

FIG. 1: represents the humin (b) formed from a compound of formula (II) prepared in situ in the process according to the invention of Example 1 and the humin (a) formed from a commercial compound of formula (II) according to Example 2.

DETAILED DESCRIPTION OF THE INVENTION

Definitions

In the present application, unless expressly indicated otherwise, all the percentages (%) shown are percentages (%) by mass.

Moreover, any interval of values denoted by the expression "between a and b" represents the range of values extending from more than a to less than b (that is to say, limits a and b excluded), whereas any interval of values denoted by the expression "from a to b" means the range of values extending from a up to b (that is to say, including the strict limits a and b).

In the present application, when an interval of values is denoted by the expression "from a to b", the interval represented by the expression "between a and b" is also and preferentially denoted.

The compounds mentioned in the description may be of fossil origin or may be biobased. In the latter case, they may be partially or completely derived from biomass or may be obtained from renewable starting materials derived from biomass. Obviously, the compounds mentioned may also originate from the recycling of already-used materials, that is to say that they may be partially or completely derived from a recycling process, or else obtained from starting materials themselves derived from a recycling process. This notably relates to polymers, plasticizers, fillers, etc.

For the purposes of the present invention, the term "monosaccharide" is understood to mean more particularly a hexose (saccharide with 6 carbon atoms) such as an aldohexose (saccharide bearing an aldehyde function in the terminal position, i.e. on carbon atom 1) or a ketohexose (saccharide bearing a ketone function on carbon atom 2). Therefore, it will in particular be allose, altrose, glucose, mannose, gulose, idose, galactose, talose, fructose, psicose, sorbose or tagatose, in D or L form. The monosaccharide will preferably be in a cyclized form.

For the purposes of the present invention, a "polysaccharide" is understood to mean a molecule comprising at least two monosaccharide molecules as defined above (referred to as monosaccharide units) linked together by a covalent bond. It may be cellulose.

For the purposes of the present invention, a "nitrone" is understood to mean a 1,3-dipolar function corresponding to the formula —C═N→O, including its mesomeric forms, capable of forming a covalent bond by a 1,3 dipolar addition to an unsaturated carbon-carbon bond.

For the purposes of the present invention, a "$C_1$-$C_x$ alkyl" is understood to mean a linear or branched, saturated hydrocarbon chain comprising 1 to x carbon atoms. Mention may be made, by way of example, of the methyl, ethyl, propyl, isopropyl, butyl, isobutyl, sec-butyl, tert-butyl, pentyl or hexyl groups.

For the purposes of the present invention, a "$C_3$-$C_{20}$ cycloalkyl" is understood to mean a saturated hydrocarbon chain comprising 3 to 20 carbon atoms. By way of example, mention may be made of cyclopropyl, cyclopentyl, cyclohexyl and cycloheptyl groups.

For the purposes of the present invention, an "aliphatic hydrocarbon chain" is understood to mean a linear or branched, saturated or unsaturated hydrocarbon chain optionally comprising one or more non-aromatic hydrocarbon rings. Preferably, it is a linear or branched, saturated hydrocarbon chain, namely an alkyl chain.

For the purposes of the present invention, an "$C_6$-$C_{20}$ aryl" is understood to mean an aromatic hydrocarbon group comprising from 6 to 20 carbon atoms, and comprising one or more fused rings, such as a phenyl or naphthyl group. Advantageously, it is the phenyl.

For the purposes of the present invention, "ambient temperature" is understood to mean a temperature within a range extending from 15° C. to 40° C., preferentially from 20° C. to 25° C., more preferentially still a temperature of 23° C.

For the purposes of the present invention, "humin" or "solids" is understood to mean the residue formed during the process for obtaining the compound of formula (I) and which is not soluble in the organic solvent used in step (i).

The addition of one or more components in "semi-continuous mode" to one or more other components is understood to mean a gradual addition, i.e. in fractions or continuously but spread out over time, of this (these) component(s) to one or more other components.

5-((2-Methyl-1H-imidazol-1-yl)methyl)furan-2-carbaldehyde will be denoted equally as compound of formula Chem. I and compound of formula (I) in the present description.

5-(Chloromethyl)furan-2-carbaldehyde will be denoted equally as compound of formula Chem. II and compound of formula (II) in the present description.

1-(5-((2-Methyl-1H-imidazol-1-yl)methyl)furan-2-yl)-N-phenylmethanimine oxide will be denoted equally as compound of formula Chem. IIIa and compound of formula (IIIa) in the present description.

5-((2-Methyl-1H-imidazol-1-yl)methyl)furan-2-yl)-N-tolylmethanimeine oxide will be denoted equally as compound of formula Chem. IIIb and compound of formula (IIIb) in the present description.

Process for Preparing 5-((2-methyl-1H-imidazol-1-yl)methyl)furan-2-carbaldehyde A first subject of the invention relates to a process for preparing the compound of formula (I), also referred to as Chem. I:

[Chem. I]

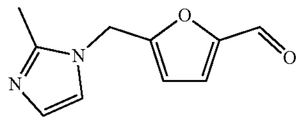

comprising the following successive steps:

(i) preparing a mixture comprising a carbohydrate, an alkali or alkaline-earth metal chloride, hydrochloric acid, water, an organic solvent and optionally a phase-transfer agent, said mixture being heated to a temperature within a range of from 35° C. to 90° C., preferentially within a range of from 45° C. to 80° C., particularly preferably within a range of from 55° C. to 75° C., said organic solvent being a water-insoluble polar aprotic solvent, and said carbohydrate being a monosaccharide, a polysaccharide or a mixture thereof, (ii) cooling the mixture obtained from step (i) to give a cooled mixture, separating the cooled mixture into an aqueous phase and an organic phase, and recovering the organic phase, said organic phase comprising the organic solvent and a compound of formula (II), also referred to as Chem. II:

[Chem. II]

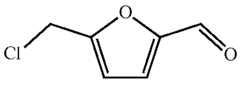

(iii) mixing 2-methylimidazole and the organic phase obtained from step (ii), the 2-methylimidazole being in molar excess relative to the compound of formula (II);

(iv) recovering the compound of formula (I) formed following step (iii).

The compound of formula (I) is 5-((2-methyl-1H-imidazol-1-yl)methyl)furan-2-carbaldehyde. The compound of formula (II) is 5-(chloromethyl)furan-2-carbaldehyde.

Step (i)

According to the present invention, the compound of formula (II) is obtained from a mixture comprising a carbohydrate, an alkali or alkaline-earth metal chloride, hydrochloric acid, water, an organic solvent which is a water-insoluble polar aprotic solvent, and optionally a phase-transfer agent, said mixture being heated to a temperature within a range of from 35° C. to 90° C., preferentially within a range of from 45° C. to 80° C., particularly preferably within a range of from 55° C. to 75° C., said carbohydrate being a monosaccharide, a polysaccharide or a mixture thereof.

When the carbohydrate is a polysaccharide, it will first be hydrolyzed to monosaccharides in the acid medium (hydrochloric acid) of step (i).

The monosaccharide is then converted into the compound of formula (II) in the presence of the alkali or alkaline-earth metal chloride in the acid medium of step (i).

The carbohydrate may be a polysaccharide such as inulin, cellulose or hemicellulose.

Preferably, the polysaccharide is cellulose.

Preferably, the carbohydrate may be a monosaccharide such as fructose, sorbose or glucose.

Preferably, the monosaccharide is fructose such as D-fructose.

According to one embodiment, the carbohydrate is fructose or cellulose.

Preferably, the carbohydrate such as fructose is a biobased carbohydrate. For the purposes of the present invention, a "biobased carbohydrate" is understood to mean a carbohydrate obtained from biomass which may be differentiated from a carbohydrate synthesized from fossil starting materials by the methods described in the standard ASTM D6866-12.

The organic solvent is a polar aprotic solvent that is insoluble in water, i.e. the mixture of the organic solvent and water is biphasic. It may be toluene, an aryl halide (e.g. chlorobenzene) or a ketone such as a di(($C_1$-$C_6$)alkyl) ketone (e.g. methyl isobutyl ketone).

Preferably, the organic solvent is toluene.

The use of toluene as organic solvent in step (i) is particularly preferred because the applicant has observed unexpectedly that the reaction for obtaining the compound of formula (I) in toluene leads to the generation of humin having a structure different from that of the humin formed using solvents other than toluene (such as DMF and isopropanol). This humin is less tacky than that formed in the other solvents: It can thus be removed more easily during the downstream purification operations of the compound of formula (I). In addition, the less tacky nature of the humin limits the fouling of the equipment and the cleaning thereof is facilitated.

Toluene is also a more acceptable alternative to the solvents of the prior art.

The temperature of the mixture comprising a carbohydrate, an alkali or alkaline-earth metal chloride, hydrochloric acid, water, an organic solvent which is a water-insoluble polar aprotic solvent and optionally a phase-transfer agent is selected so as to maximize the yield and limit parasitic chemistry. Too high a temperature can lead to rapid degradation of the compound of formula (II) formed, a decrease in selectivity and in yield. Too low a temperature (below 30° C.) can lead to a low yield of compound of formula (II).

The temperature of the mixture may thus be within a range of from 35° C. to 90° C., preferentially from 45° C. to 80° C., particularly preferably from 55° C. to 75° C.

The amount of hydrochloric acid is advantageously within a range of from 3 to 7 molar equivalents, preferentially from 3.5 to 6 molar equivalents, particularly preferably from 4 to 5 molar equivalents relative to the amount of monosaccharide units present in the carbohydrate.

The amount of chloride ions supplied by the alkali or alkaline-earth metal chloride is advantageously within a range of from 1.2 to 2.6 molar equivalents, preferentially within a range of from 1.6 to 2.4 molar equivalents, particularly preferably within a range of from 1.7 to 2.2 molar equivalents relative to the amount of monosaccharide units present in the carbohydrate.

According to one embodiment, the alkali metal or alkaline-earth metal chloride is chosen from magnesium chloride and lithium chloride, and is preferentially magnesium chloride. The magnesium chloride can be hydrated, in particular in hexahydrate form.

When the alkali metal or alkaline-earth metal chloride is magnesium chloride, the amount of magnesium chloride is advantageously within a range of from 0.6 to 1.3 molar equivalents, preferentially within a range of from 0.8 to 1.2 molar equivalents, particularly preferably within a range of from 0.85 to 1.1 molar equivalents relative to the amount of monosaccharide units present in the carbohydrate.

When the alkali metal or alkaline-earth metal chloride is lithium chloride, the amount of lithium chloride is advantageously within a range of from 1.2 to 2.6 molar equivalents, preferentially within a range of from 1.6 to 2.4 molar equivalents, particularly preferably within a range of from 1.7 to 2.2 molar equivalents relative to the amount of monosaccharide units present in the carbohydrate.

Optionally, according to a variant of the process, step (i) may comprise a phase-transfer agent. The use of a phase-transfer agent can make it possible to improve the yield of the reaction for obtaining the compound of formula (II). The phase-transfer agent is advantageously a quaternary ammonium halide, for example a tetra($C_1$-$C_{20}$ alkyl)ammonium halide (e.g. bromide), preferentially hexadecyltrimethylammonium bromide, the amount of which is advantageously within a range of from 0.001 to 0.01 molar equivalents relative to the amount of monosaccharide units present in the carbohydrate.

The mixture of carbohydrate, an alkali metal or alkaline-earth metal chloride, hydrochloric acid, water, organic solvent and optionally a phase-transfer agent is preferentially obtained in a semi-continuous mode, that is to say by carrying out the addition, in semi-continuous mode, as defined above, of one portion of the components of the mixture to the other portion of the components of the mixture.

For example, a composition comprising the carbohydrate, the alkali or alkaline-earth metal chloride, the hydrochloric acid, the water, and optionally the phase-transfer agent may be added in semi-continuous mode to the organic solvent. The addition is advantageously carried out in semi-continuous mode in order to limit the concentration of the carbohydrate in the organic phase and consequently the side reactions. The composition comprising the carbohydrate, the alkali or alkaline-earth metal chloride, the hydrochloric acid, the water, and optionally the phase-transfer agent can be prepared by adding the carbohydrate, preferably at room temperature, to a mixture comprising the alkali or alkaline-earth metal chloride, the hydrochloric acid and optionally the phase-transfer agent. The carbohydrate may also be added alone or in solution in water to a mixture containing the other reactants.

Conversely, the components of the composition may be added to the carbohydrate.

A mixture comprising the alkali or alkaline-earth metal chloride, the hydrochloric acid and optionally the phase-transfer agent may also be added to a solution of organic solvent and carbohydrate.

A hydrochloric acid solution may also be added to a mixture comprising the carbohydrate, the organic solvent, the alkali metal or alkaline-earth metal chloride, the water and optionally the phase-transfer agent.

According to one embodiment, step (i) of the process comprises the following steps:

(i1) preparing a composition comprising the carbohydrate, the alkali or alkaline-earth metal chloride, the hydrochloric acid, the water, and optionally the phase-transfer agent; and (i2) adding, preferably in semi-continuous mode, the composition obtained from step (i1) to the organic solvent heated to a temperature within a range of from 35° C. to 90° C., in particular from 45° C. to 80° C., preferentially from 55° C. to 75° C.

According to another embodiment, step (i) of the process comprises the following steps:

(i1) adding the carbohydrate to the organic solvent heated to a temperature within a range of from 35° C. to 90° C., in particular from 45° C. to 80° C., preferentially from 55° C. to 75° C.;

(i2) preparing a composition comprising the alkali or alkaline-earth metal chloride, the hydrochloric acid, the water, and optionally the phase-transfer agent; and (i3) adding, preferably in semi-continuous mode, the composition obtained from step (i2) to the heated organic solvent comprising the carbohydrate obtained from step (i1).

According to another embodiment, step (i) of the process comprises the following steps:

(i1) preparing a composition comprising the carbohydrate and the water;

(i2) preparing a composition comprising the organic solvent, the hydrochloric acid, the alkali or alkaline-earth metal chloride, and optionally the phase-transfer agent, said composition being heated to a temperature within a range of from 35° C. to 90° C., in particular from 45° C. to 80° C., preferentially from 55° C. to 75° C.; and (i3) adding, preferably in semi-continuous mode, the composition obtained from step (i1) to the heated composition obtained from step (i2).

According to another embodiment, step (i) of the process comprises the following steps:

(i1) preparing a composition comprising the organic solvent, the hydrochloric acid, the alkali or alkaline-earth metal chloride, the water and optionally the phase-transfer agent, said composition being heated to a temperature within a range of from 35° C. to 90° C., in particular from 45° C. to 80° C., preferentially from 55° C. to 75° C.; and (i2) adding the carbohydrate to the heated composition obtained from step (i1).

According to another embodiment, step (i) of the process comprises the following steps:

(i1) preparing a composition comprising the carbohydrate, the organic solvent, the alkali or alkaline-earth metal chloride, and optionally the phase-transfer agent, said composition being heated to a temperature within a range of from 35° C. to 90° C., in particular from 45° C. to 80° C., preferentially from 55° C. to 75° C.; and (i2) adding, preferably in semi-continuous mode, a solution of hydrochloric acid to the heated composition obtained from step (i1).

The mixture is heated for a period of time that makes it possible to optimize the yield of the compound of formula (II) while limiting the formation of by-products and decomposition products of said compound. The duration of step (i) is also adjusted depending on the nature of the carbohydrate. Thus, in the case of a process carried out with a polysaccharide such as cellulose as carbohydrate, the duration of step (i) is adjusted so as also to optimize the prior step of hydrolysis of the polysaccharide to monosaccharide.

In the case of a process carried out in a 500 ml laboratory reactor with fructose as carbohydrate, the duration of step (i) is typically less than 90 minutes.

Preferably, during step (i), the mixture is stirred at a stirring speed which makes it possible to ensure good mixing of the components while limiting the shear. Thus, in the case of a process carried out in a 500 ml laboratory reactor, the stirring speed is within a range of from 300 to 1000 rpm.

Step (ii)

Step (ii) makes it possible to recover the organic phase containing the compound of formula (II) formed in step (i), without however isolating this compound. In fact, owing to its hydrophobic nature, the compound of formula (II) partitions predominantly into the organic phase of the mixture based on the organic solvent, namely a water-insoluble polar aprotic solvent such as toluene.

Thus, the mixture resulting from step (i) is cooled, ideally to room temperature, before separating it into an organic phase and an aqueous phase, and recovering the organic phase which contains the compound of formula (II).

Preferably, a filtration step is carried out after the cooling step and before the separation step in order to remove the solids present.

The solids are advantageously washed with the organic solvent of the preceding step, namely a water-insoluble polar aprotic solvent such as toluene.

These solids, also referred to as humin, consist predominantly of oligomers of monosaccharide units and/or of furan derivatives.

The organic phase is then advantageously treated using steps well known to those skilled in the art. Thus, for example, the organic phase is washed, once or several times, with a saturated aqueous NaCl solution.

The organic phase may optionally be dried, for example by contacting with $MgSO_4$, by azeotropic distillation or by passing through a drying membrane/cartridge or over a sieve.

As described above, the compound of formula (II) partitions predominantly into the organic phase and is not isolated before use in step (iii), which constitutes an improvement of the existing process which required additional time-consuming separation and purification steps. In addition to the quality of the humin, which is different in the process of the invention, the applicants have also noted that the amount of humin formed in the context of the process according to the invention is minimized (maximum 30% w/w (w/w=weight/weight) to 40% w/w compared to the compound of formula (II)) when the organic solvent is a water-insoluble polar aprotic solvent such as toluene, which limits equipment cleaning and maintenance operations, which can be time-consuming due to the tacky and fouling properties of humin.

The applicants have furthermore observed that the organic phase obtained in step (ii) is stable if it is stored at low temperature (typically in a range of from −20° C. to +4° C.) for at least 3 days and for several hours at 70° C. In the literature, however, it is reported that the isolated compound of formula (II) is not very stable without stabilizing agent and decomposes rapidly at room temperature: it must thus be stored cold (−5° C.) and in the presence of additives.

At the end of this step, the compound of formula (II) is obtained in a yield of greater than 30%, in particular greater than 50%, preferably greater than 60%.

Step (iii)

Step (iii) of synthesis of the compound of formula (I) from the compound of formula (II) is carried out in the same organic solvent, namely a water-insoluble polar aprotic solvent such as toluene, such as the one from step (i), the latter being present in the organic phase recovered in step (ii) and containing the compound of formula (II).

WO 2020/249631 describes the synthesis of the compound of formula (I) from compound (II) in DMF, which has the drawback of having a certain toxicity.

U.S. Pat. No. 4,729,851 also describes the synthesis of a molecule similar to the compound of formula (I), except that it comprises an imidazole and not a methylimidazole. The preparation of this compound is carried out in chloroform, which is less acceptable from an HSE standpoint than the organic solvent, namely a water-insoluble polar aprotic solvent, in particular toluene, used in step (iii).

The use in step (iii) of the same organic solvent, namely a water-insoluble polar aprotic solvent such as toluene, as in step (i) further enables the organic phase comprising the organic solvent and the compound of formula (II) obtained from step (ii) to be used directly, thus avoiding the steps of separating and purifying the compound of formula (II).

The compound of formula (I) is obtained by reacting 2-methylimidazole and the organic phase obtained from step (ii), the 2-methylimidazole being in molar excess relative to the compound of formula (II).

According to one embodiment, the amount of 2-methylimidazole during step (iii) is within a range of from 2.0 to 3.0 molar equivalents, preferably in a range of from 2.0 to 2.5, more preferentially from 2.1 to 2.2 molar equivalents relative to the amount of the compound of formula (II).

The amount of 2-methylimidazole to be used during step (iii) will more particularly be calculated from the concentration of compound of formula (II) in the organic phase obtained from step (ii) determined by an assay, for example by NMR.

The mixing of 2-methylimidazole and the organic phase containing the non-isolated compound of formula (II) obtained from step (ii) is preferably prepared in semi-continuous mode. The 2-methylmidazole is added in semi-continuous mode to said organic phase or else said organic phase is added in semi-continuous mode to the 2-methylmidazole.

According to one embodiment, step (iii) comprises the following steps:

(iii1) adding, preferably in semi-continuous mode, a fraction of the organic phase obtained from step (ii) to the 2-methylimidazole at room temperature;

(iii2) heating the composition obtained from step (iii1) to a temperature within a range of from 50° C. to 90° C., preferably from 60° C. to 80° C., more preferentially from 65° C. to 75° C.; and (iii3) adding, preferably in semi-continuous mode, the remaining fraction of the organic phase obtained from step (ii) to the heated composition obtained from step (iii2).

According to another embodiment, step (iii) comprises the following step:

(iii1) adding, preferably in semi-continuous mode, the 2-methylimidazole to the organic phase obtained from step (ii) heated to a temperature within a range of from 50° C. to 90° C., preferably from 60° C. to 80° C., preferably from 65° C. to 75° C.

Advantageously, in this embodiment, the 2-methylimidazole can be added in the form of a composition comprising the 2-methylimidazole and a polar non-nucleophilic solvent. This allows a controlled semi-continuous addition of the 2-methylimidazole. The polar non-nucleophilic solvent may be an alcoholic solvent such as isopropanol.

The semi-continuous addition time according to any one of the preceding embodiments is advantageously within a range of from 2 hours to 8 hours, preferably from 3 hours to 6 hours.

Advantageously, the mixture obtained during step (iii) comprising the 2-methylimidazole and the organic phase obtained from step (ii) is maintained at a temperature within a range of from 50° C. to 90° C., more preferentially from 60° C. to 80° C., more preferentially from 65° C. to 75° C., preferably for a period of time within a range of from 4 to 6 hours, notably from the end of the addition, in particular in semi-continuous mode, of the 2-methylimidazole or of the organic phase obtained from step (ii).

The preparation of the compound of formula (II) according to the invention makes it possible, unexpectedly, to synthesize the compound of formula (I) with yields greater than those obtained from a commercial compound of formula (II), such as for example the product sold by ABCR.

Specifically, as illustrated in Examples 1 and 2, the use of a commercial compound of formula (II) such as the one from ABCR results in a yield of compound (I) that is three times lower under the same operating conditions. The commercially available compounds of formula (II) contain impurities, in particular acetic acid, which differ from those of the compound of formula (II) prepared in situ in the process according to the invention. These impurities show that the synthetic pathways are different. In addition, these appear to have a negative impact on yield, with the formation of a larger amount of humin. It is in fact that acidic impurities such as Brönsted acids can have an impact on the yield of addition product and the formation of polymeric by-products, as is described in U.S. Pat. No. 4,729,851A.

Moreover, the humin formed during step (iii) from a compound of formula (II) prepared in situ in the process according to the invention has a less fouling nature than the humin formed from a commercial compound of formula (II). This is illustrated in FIG. 1 comparing the humin (b) formed from a compound of formula (II) prepared in situ in the process according to the invention of Example 1 and the humin (a) formed from a commercial compound of formula (II) according to Example 2.

Steps (i) to (iii) are therefore interdependent and must all be carried out to ensure a maximum yield, with savings in individual steps and to avoid the presence of impurities present in the commercial compounds of formula (II) which have a negative influence on the yield.

Step (iv)

On conclusion of step (iii), a portion of the compound of formula (I) is trapped in the solid precipitate which forms during the reaction. The compound of formula (I) present in this precipitate can be recovered by techniques well known to those skilled in the art, such as, for example, by filtration of the mixture obtained from step (iii) and successive washings of the filtration residue (commonly referred to as cake) with the organic solvent, namely a water-insoluble polar aprotic solvent such as toluene, from step (i), to maximize the recovery of this compound of formula (I) in the filtrate.

The compound of formula (I) can then be separated from the filtrate by techniques well known to those skilled in the art, such as by crystallization. If the purity is insufficient, additional purification operations are possible, such as liquid-liquid extractions of organic solvent/water type. The dichloromethane/water pair for the liquid/liquid extraction is particularly preferred.

On conclusion of this step (iv), the compound of formula (I) is recovered with a yield of greater than 30%, preferably greater than 40%. It is obtained with a molar purity of greater than 90%.

Process for Synthesizing a Nitrone of Formula (III).

The process for preparing the compound of formula (III) below, also referred to as Chem. III:

[Chem. III]

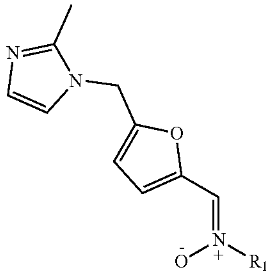

comprises the following steps:

(a) preparing a compound of formula (I) by a process according to the invention as described above;

(b) reacting the compound of formula (I) obtained in step (a) with a compound of formula $R_1$—$NO_2$ in the presence of a reducing agent, preferentially zinc, in order to form the compound of formula (III); and (c) recovering the compound of formula (III); where $R_1$ is selected from the group consisting of linear or branched $C_1$-$C_{20}$ alkyls; $C_3$-$C_{20}$ cycloalkyls optionally substituted with one or more preferably saturated, linear or branched aliphatic hydrocarbon chains; and $C_6$-$C_{20}$ aryls optionally substituted with one or more preferably saturated, linear or branched aliphatic hydrocarbon chains; preferably $R_1$ is a $C_6$-$C_{20}$ aryl optionally substituted with one or more $C_1$-$C_6$ alkyls, preferably one or more $C_1$-$C_3$ alkyls; more preferentially still $R_1$ is a $C_6$ aryl optionally substituted with one or more $C_1$-$C_6$ alkyls, preferably one or more $C_1$-$C_3$ alkyls.

Among the compounds of formula (III), those in which $R_1$ is a $C_6$-$C_{20}$ aryl optionally substituted with one or more preferably saturated, linear or branched aliphatic hydrocarbon chains are preferred; preferably $R_1$ is a $C_6$-$C_{20}$ aryl optionally substituted with one or more $C_1$-$C_6$ alkyls, preferably one or more $C_1$-$C_3$ alkyls; preferably $R_1$ is a $C_6$ aryl optionally substituted with one or more $C_1$-$C_6$ alkyls, preferably one or more $C_1$-$C_3$ alkyls. More preferentially still, among the compounds of formula (III), the compounds of formulae (IIIa) and (IIIb) are preferred.

The compound of formula (IIIa), also referred to as Chem. IIIa, is 1-(5-((2-methyl-1H-imidazol-1-yl)methyl)furan-2-yl)-N-phenylmethanimine oxide.

[Chem. IIIa]

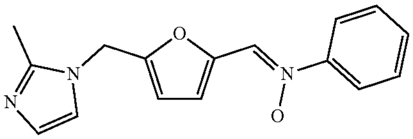

The compound of formula (IIIb), also referred to as Chem. IIIb, is 5-((2-methyl-1H-imidazol-1-yl)methyl)furan-2-yl)-N-tolylmethanimine oxide.

[Chem. IIIb]

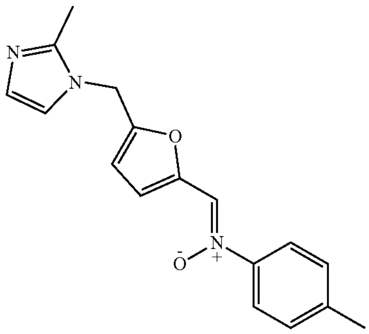

The process according to the invention makes it possible to synthesize the compound of formula (III) without it being necessary to separate the product $R_1$—NH—OH obtained from the compound $R_1$—$NO_2$, with $R_1$ being as defined above, before reaction with the compound of formula (I), but by generating it in situ, which simplifies the synthesis process.

Step (b)

Said step (b) of the process according to the invention is advantageously carried out in the presence of a reducing agent.

Preferably, the reducing agent is chosen from zinc and hydrogen, preferentially zinc. According to a specific embodiment of the invention, the amount of reducing agent is from 1.5 to 6 molar equivalents, preferably from 2 to 5 molar equivalents, relative to the amount of compound of formula (I).

When the reducing agent is hydrogen, step (b) will advantageously also be carried out in the presence of a metal hydrogenation catalyst known to those skilled in the art, whether it is supported (for example Pd/C, Pt/C, Ru/C or Rh/C) or unsupported (such as for example Tebbe's reagent or Raney nickel).

When the reducing agent is zinc, step (b) will advantageously be carried out in the presence of an acid, advantageously chosen from an organic acid (e.g. acetic acid, propionic acid, or any alkylated organic carboxylic acid) and a weak acid salt (e.g. an ammonium salt such as ammonium chloride). Preferably, step (b) is carried out, when the reducing agent is zinc, in the presence of an ammonium salt, such as ammonium chloride.

Said step (b) is also advantageously carried out in the presence of a solvent.

Advantageously, the solvent is chosen from water, an alcohol solvent (e.g. ethanol, isopropyl alcohol), an ether solvent (e.g. tetrahydrofuran, dioxane), a nitrile solvent (acetonitrile, etc.) and mixtures thereof; preferably chosen from water, an alcohol solvent and mixtures thereof. When a mixture of solvents is used, the mixture is advantageously monophasic. The mixture of solvents is advantageously a water/alcohol solvent mixture such as a water/ethanol mixture.

According to a specific embodiment of the invention, the solvent is a water/ethanol mixture, advantageously with a water/ethanol ratio as percentage by weight within a range of from 1/99 to 50/50, preferentially within a range of from 5/95 to 30/70, particularly preferably in a range of from 7/93 to 15/85. The water/ethanol mixture is acceptable from an HSE standpoint and enables a maximized yield.

The compound of formula $R_1$—$NO_2$ used in step (b) is a compound in which $R_1$ is selected from the group consisting of linear or branched $C_1$-$C_{20}$ alkyls; $C_3$-$C_{20}$ cycloalkyls optionally substituted with one or more preferably saturated, linear or branched aliphatic hydrocarbon chains; and $C_6$-$C_{20}$ aryls optionally substituted with one or more preferably saturated, linear or branched aliphatic hydrocarbon chains.

Preferably, the compound of formula $R_1$—$NO_2$ used in step (b) is a compound in which $R_1$ is a $C_6$-$C_{20}$ aryl optionally substituted with one or more $C_1$-$C_6$ alkyls, preferably one or more $C_1$-$C_3$ alkyls.

More preferentially still, the compound of formula $R_1$—$NO_2$ used in step (b) is a compound in which $R_1$ is a $C_6$ aryl optionally substituted with one or more $C_1$-$C_6$ alkyls, preferably one or more $C_1$-$C_3$ alkyls.

According to one embodiment, step (b) comprises the following steps:

(b1) preparing a composition comprising the compound of formula (I) obtained in step (a), an ammonium salt such as ammonium chloride and a water/ethanol mixture, advantageously with a water/ethanol ratio as percentage by weight within a range of from 1/99 to 50/50, preferentially within a range of from 5/95 to 30/70, particularly preferably in a range of from 7/93 to 15/85;

(b2) adding the compound of formula $R_1$—$NO_2$ with $R_1$ as defined above, to the composition obtained in step (b1), preferentially in an amount within a range of from 0.80 to 1.20 molar equivalents, preferentially from 0.90 to 1.10 molar equivalents, particularly preferably from 0.95 to 1.05 molar equivalents, relative to the amount of the compound of formula (I); and (b3) adding, preferably in semi-continuous mode, zinc to the composition obtained in step (b2) maintained at a temperature in a range of from 15° C. to 25° C., preferentially from 15° C. to 22° C., during the addition step.

According to one embodiment, during step (b1), a solution of ammonium salt in water is added to a solution of the compound of formula (I) in ethanol.

In order to control the temperature during mixing and guarantee a maximum yield, the components are preferably added in the following order: the compound of formula $R_1$—$NO_2$ and thenzinc are added, preferably in semi-continuous mode, to the water/ethanol mixture comprising the compound of formula (I) and the ammonium salt.

Step (b3) is advantageously carried out at a controlled temperature within a range of from 15° C. to 25° C., preferentially from 15° C. to 22° C., preferably around 20° C., in order to limit the formation of by-products.

According to one embodiment, the composition obtained from step (b3), before carrying out step (c), is maintained at a temperature within a range of from 15° C. to 25° C., preferentially from 15° C. to 22° C., preferably for 4 to 6 hours from the end of the addition, preferably in semi-continuous mode, of the zinc.

Advantageously, a stoichiometric amount of compound of formula $R_1$—$NO_2$ relative to the compound of formula (I) is used. An excess of the compound $R_1$—$NO_2$ would not make it possible to improve the yield of the compound of formula (I) and would also generate by-products.

Step (c)

During step (c), the compound of formula (III) is recovered, in particular after treatment and purification steps which are conventional for those skilled in the art. For example:

- the medium is filtered and then the residue is washed with ethanol;
- the filtrates are combined and evaporated;
- the residue is taken up in an MTBE/ethyl acetate mixture and then recrystallized at room temperature.

On conclusion of this step (c), the compound of formula (III) is obtained with a yield of greater than 70% relative to the initial amount of compound of formula (I). The compound of formula (III) is advantageously obtained with a molar purity greater than 90 mol %.

Polymer Modified by Grafting of a Compound of Formula (III).

The term "modified polymer obtained by grafting" or "polymer modified by grafting" is understood to mean a polymer obtained by a grafting reaction of the compound of formula (III), the nitrone function of which is capable of forming a covalent bond with an unsaturation of the chain of the polymer.

As is known, a polymer generally comprises at least one main polymer chain. This polymer chain may be termed the main chain as long as all the other chains of the polymer are considered to be pendent chains, as mentioned in the document "Glossary of basic terms in polymer science" (IUPAC recommendations 1996), PAC, 1996, 68, 2287, page 2294.

The term "unsaturation" is understood to mean a multiple covalent bond between two carbon atoms; this multiple covalent bond may be a carbon-carbon double bond or a carbon-carbon triple bond, preferably a carbon-carbon double bond.

For the purposes of the present invention, the term "initial polymer chain" is understood to mean the chain of the polymer before the grafting reaction, this chain comprising at least one unsaturation that is capable of reacting with the compound of formula (III). The initial polymer is thus the polymer serving as the starting reagent during the grafting reaction. The grafting reaction makes it possible, starting with an initial polymer, to obtain a modified polymer.

Preferably, this initial polymer is an elastomer, i.e. a polymer having elastic properties, more preferentially still a diene elastomer.

A "diene" elastomer (or equally rubber) is understood to mean an elastomer consisting at least in part (i.e. a homopolymer or a copolymer) of repeating units derived from diene monomers, i.e. monomers bearing two conjugated or unconjugated carbon-carbon double bonds. The diene elastomer may be natural or synthetic.

The compound of formula (III), more preferentially the compound of formula (III) in which $R_1$ is a $C_6$ aryl optionally substituted with one or more $C_1$-$C_6$ alkyls, preferably one or more $C_1$-$C_3$ alkyls, more preferentially the compounds of formula (IIIa) and (IIIb), is useful as polymer-modifying agents. It may be grafted onto one or more polymers comprising at least one unsaturated carbon-carbon bond; in particular, this polymer may be an elastomer and more particularly a diene elastomer as defined previously.

The polymer then bears along the main polymer chain one or more pendent groups derived from the grafting reaction of the compound of formula (III). Advantageously, these pendent groups are distributed randomly along the main polymer chain.

According to a preferred embodiment, the molar degree of grafting of the compound of formula (III) is within a range of from 0.01% to 15%, preferably from 0.05% to 10%, more preferentially from 0.07% to 5%.

The term "molar degree of grafting" is understood to this mean the number of moles of compound of formula (III) grafted onto the polymer per 100 moles of repeating unit constituting the initial polymer. The molar degree of grafting can be determined by conventional polymer analysis methods, for instance NMR analysis.

The modified polymer is obtained according to a process comprising a step of grafting, onto an initial polymer comprising at least one unsaturation, of the compound of formula (III) by [3+2] cycloaddition of the nitrone function of the compound of formula (III) onto said unsaturation.

The mechanism of this cycloaddition is notably illustrated in document WO 2012/007441. During this reaction, said compound of formula (III) forms covalent bonds with the polymer chain.

According to one embodiment, the grafting of the compound of formula (III) may be carried out in bulk, for example in an extruder, an internal mixer or an external mixer, such as an open mill.

According to another embodiment, the process for preparing a modified polymer may be performed in solution, for example continuously or batchwise. The polymer thus obtained by grafting may be separated from its solution by any type of means known to those skilled in the art and in particular by a steam stripping operation.

Preferably, this initial polymer is an elastomer, more preferentially still is a diene elastomer.

Composition

The modified polymer obtained by grafting the compound of formula (III) as defined above (including its preferred forms) may be used in a composition further comprising at least one additive.

The additives that may be used in the composition according to the invention may be plasticizers (such as plasticizing oils and/or plasticizing resins), fillers (reinforcing or non-reinforcing fillers), pigments, protective agents (such as antiozone waxes, chemical antiozonants, antioxidants and antifatigue agents), reinforcing resins (as described, for example, in patent application WO 02/10269), a crosslinking system, for example based on sulfur and other vulcanizing agents, and/or peroxide and/or bismaleimide. Preferably, this additive is a reinforcing filler, more preferentially this additive is an inorganic reinforcing filler, and even more preferentially this additive is a silica.

BIBLIOGRAPHIC REFERENCES

Green Chem., 2011, 13, 1114-1117
Eur. J. Org. Chem. 2011, 1266-1270
Renewable Energy. 2016, 85, 994-1001
ACS Sustainable Chem. Eng. 2019, 7, 5588-5601
Angew Chem, Int Ed, 2008, 47, 7924-7926
Carbohydrate Research, 187(1), 15-23; 1989
Organic Syntheses, Coll. Vol. 4. p. 57 (1925)

EXAMPLES

The examples which follow make it possible to illustrate the invention; however, the invention shall not be limited to these examples alone.

Characterization of the Molecules.

The conversion, the product assay yield, the structural analysis and also the determination of the molar purities of the synthesis molecules are carried out by NMR analysis. The spectra are acquired on a 3400 MHz Bruker Avance spectrometer equipped with a 5 mm BBFO Z-grad "broad band" probe. The quantitative $^1H$ NMR experiment uses a simple 300 pulse sequence and a repetition time of 3 seconds between each of the 64 acquisitions. The samples are dissolved in a deuterated solvent, deuterated dimethyl sulfoxide (DMSO) unless otherwise indicated. The deuterated solvent is also used for the lock signal. For example, calibration is performed on the signal of the protons of the deuterated DMSO at 2.44 ppm relative to a TMS reference at 0 ppm. The $^1H$ NMR spectrum coupled with the 2D $^1H/^{13}C$ HSQC and $^1H/^{13}C$ HMBC experiments enable the structural determination of the molecules (cf. assignment tables). The molar quantifications are carried out from the quantitative 1D $^1H$ NMR spectrum.

The concentration and therefore the yield of compound (II) in solution is obtained by the same technique, by external calibration by adding a known amount of a product, the signals of which do not interfere with the signals of the species present, such as, for example, benzyl benzoate.

Example 1: Synthesis of 5-((2-methyl-1H-imidazol-1-yl)methyl)furan-2-carbaldehyde According to the process in accordance with the invention The example below is a preferred embodiment of the invention. Other embodiments are possible. The compound of formula (I) is synthesized according to steps (i) to (iv) of the process according to the invention starting from D-fructose.

D-fructose is purchased from Aldrich under the reference F0127.

Step (i):

Preparation of the Salts in Hydrochloric Acid 203 g of $MgCl_2$ hexahydrate (1 equiv. relative to D-fructose (equiv.=equivalent)) are solubilized in a concentrated 37% hydrochloric acid solution (423 g, 4.3 equiv. of HCl relative to D-fructose) at room temperature (T=23° C.), with stirring, until a colourless transparent homogeneous solution is obtained (concentration of $MgCl_2$ hexahydrate in the acid: 2.3 mol %). Next, hexadecyl(trimethyl)ammonium bromide (1.8 g, 0.5 mol % relative to D-fructose) is solubilized in the $MgCl_2$/HCl solution until a transparent and colourless homogeneous solution is obtained. The D-fructose (180 g, 1 equiv.) is gradually solubilized in the preceding solution by portionwise additions at room temperature (addition and solubilizing time: 30 minutes).

The solution obtained is referred to as Sol. A (concentration of D-fructose in Sol. A: 2.2 mol %). This Sol. A solution is then poured into a dropping funnel.

Synthesis of 5-(chloromethyl)furan-2-carbaldehyde (compound of formula (II))

Toluene (1040 g, i.e. 5.8 kg/kg of D-fructose) is introduced into a 500-ml reactor in order to obtain a solution referred to as Sol. B. The Sol. B solution is heated to 70° C. and with stirring at 700 rpm. The Sol. A solution is added dropwise to the Sol. B solution over a period of 20 min. The reaction mixture is then maintained at a temperature of 70° C. for 20 minutes. The formation of a black powder in the medium is observed.

The reaction is monitored by thin layer chromatography (TLC) using a 90/10 (vol/vol) $CH_2Cl_2$/MeOH mixture at as elution solvent. Visualization is carried out with an iodine/silica mixture. The retention factor of 5-(chloromethyl)furan-2-carbaldehyde is 0.84 (Rf(compound of formula (II) =0.84) and the formation of this compound is also verified by $^1$H NMR.

Step (ii)

Recovery of the Organic Phase Comprising the Solvent and 5-(Chloromethyl)Furan-2-Carbaldehyde (Compound of Formula (II))

After cooling to room temperature (T=23° C.), the reaction mixture from step (i) is filtered through a Büchner funnel under vacuum. The solid (black powder) is washed with toluene three times. The mass of toluene added to each rinsing is around 5% by mass of the total reaction volume, i.e. 100 g, then the solid is removed.

The two-phase filtrate composed of an upper organic phase of brown/red colour (34% v/v) and a lower aqueous phase of yellow colour (66% v/v) is recovered. After settling and separating, the upper organic phase is recovered. The aqueous phase is not retained.

The organic phase is washed with brine (NaCl concentration ~37% by mass in distilled water) until the aqueous phase has a pH of greater than or equal to 1, preferably greater than or equal to 5. A person skilled in the art will know how to adjust the number of washes/extractions of the organic phase as a function of the size of the reactor (cf. Table 1). The mass ratio: m(organic phase)/(m(brine phase)) 2.5. The solutions are left to settle after each wash.

TABLE 1

| | Organic phase/brine mass ratio | pH of aqueous phase |
|---|---|---|
| 1st extraction | 2.5 | 1 |
| 2nd extraction | 2.5 | 2 |
| 3rd extraction | 2.5 | 5 |
| 4th extraction | 2.5 | / |
| 5th extraction | 2.5 | / |

On conclusion of this step (ii), the yield of 5-(chloromethyl)furan-2-carbaldehyde obtained from D-fructose in this example is 69% (101 g, assayed by $^1$H NMR).

Step (iii): Alkylation of the Non-Isolated Compound of Formula (II) with 2-Methylimidazole 2-Methylimidazole (1.5 mol, 119 g, i.e. 2.1 equiv. relative to the compound of formula (II), the concentration of which is determined in the Sol. C solution) is introduced at room temperature (T=23° C.) into the 500-ml reactor.

20% of the Sol. C solution is added. dropwise and at room temperature. No exothermicity was observed during the addition. When the 2-methylimidazole is solubilized in the reaction medium, this reaction medium is heated to 70° C. The addition of the residual 80% of the Sol. C solution is then continued over a period of 2 hours. After the end of the addition, the reaction medium is maintained at a temperature of 70° C. for 5 hours with stirring. The reaction mixture obtained on conclusion of this step, referred to as Sol. D, is in the form of a liquid phase with a black precipitate.

The reaction is monitored by TLC (Rf(compound of formula (I))=0.6) with a 90/10 (vol/vol) $CH_2Cl_2$/MeOH mixture at as elution solvent. Visualization of the compound of formula (I) is carried out under a UV lamp at a wavelength of 254 nm.

Step (iv): Recovery of 5-((2-methyl-1H-imidazol-1-yl)methyl)furan-2-carbaldehyde (Compound of formula (I))

The Sol. D reaction mixture is left to settle while maintaining the temperature at 70° C.; then the clear yellow supernatant phase is recovered, for example by suction.

The residual black deposit in the reactor is washed 3 times with toluene, stirring for 30 minutes at 70° C. each time. The mass of toluene added for each wash corresponds to approximately 40% to 50% of the mass of the complete reaction medium (Sol. D), i.e. 450 g of toluene. The supernatants are recovered each time after settling. The organic phases (i.e. the initial supernatant phase and the organic phases resulting from the toluene washes) are combined together and are placed at −20° C. for crystallization for a few hours. The solution is filtered in order to recover crystals of orangey-yellow or white colour on the one hand and the filtrate on the other hand. The filtrate is brought to −20° C. for a new crystallization. It is filtered again and the crystals are recovered. The black deposit obtained from the washes is dried, and it is then verified by $^1$H NMR in $CDCl_3$ that it does not contain any compound of formula (I). After verification, the black deposit is discarded.

All the crystals are dried under vacuum at 40° C. The dry crystals are yellow or white in colour and are subjected to $^1$H NMR analysis in $CDCl_3$.

The black deposit on conclusion of step (iv) is a finely divided solid, such as a powder (see FIG. 1(*b*)).

The compound of formula (I) synthesized from the non-isolated compound of formula (II) from step (ii) is obtained in a yield of 46% (60 g), with a molar purity of greater than 90%, determined by $^1$H NMR in $CDCl_3$. The peaks of the $^1$H and $^{13}$C NMR spectra are detailed in Table 2 below with the numbering of the carbon atoms presented on the Chem. I-NMR formula.

TABLE 2

[Chem. I-NMR]

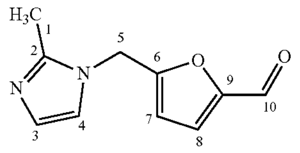

| No. | δ $^1$H (ppm) | δ $^{13}$C (ppm) |
|---|---|---|
| 1 | 2.42 | 13.5 |
| 2 | / | 144.7 |

TABLE 2-continued

[Chem. I-NMR]

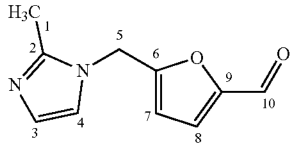

| No. | δ $^{1}H$ (ppm) | δ $^{13}C$ (ppm) |
|---|---|---|
| 3 | 7.18 | 127.3 |
| 4 | 6.85 | 119.7 |
| 5 | 5.28 | 46.4 |
| 6 | / | 153.3 |
| 7 | 6.55 | 111.8 |
| 8 | 7.35 | 122.1 |
| 9 | / | 152.9 |
| 10 | 9.59 | 177.5 |

Example 2: Synthesis of 5-((2-methyl-1H-imidazol-1-yl)methyl)furan-2-carbaldehyde According to a Process not in Accordance with the Invention In this example, 5-((2-methyl-1H-imidazol-1-yl)methyl) furan-2-carbaldehyde (compound of formula (I)) is synthesized from 5-(chloromethyl)furan-2-carbaldehyde sold by ABCR.

This synthesis corresponds to steps (iii) to (iv) of the process of the invention, with the difference that the 5-((2-methyl-1H-imidazol-1-yl)methyl)furan-2-carbaldehyde does not originate from step (ii) of the process but was purchased from ABCR. A commercial product is therefore used as starting material for step (iii) and not the Sol. C solution of the process of the invention.

Thus, 10 g of the compound of formula (II) (CAS 1623-88-7), sold by ABCR (under the reference "AB460845", purity 95%) was solubilized in 100 g of toluene. Steps (iii) and (iv) were then carried out under the same conditions described in Example 1 above, adjusting the amounts of the reactants and solvents introduced, while retaining the same molar and/or weight ratios depending on the case. The black deposit obtained on conclusion of step (iv) is a pasty solid (see FIG. 1(*a*)). This impurity is more difficult to remove than the powdery black deposit obtained with the process of the invention. On conclusion of step (iv), the yield of the compound of formula (I) obtained from the commercial compound of formula (II) is 14% (2.1 g), with a molar purity equal to 80%, determined by $^{1}H$ NMR in $CDCl_3$. The peaks of the $^{1}H$ and $^{13}C$ NMR spectra are detailed in Table 3 below with the numbering of the carbon atoms presented on the Chem. I-NMR formula.

TABLE 3

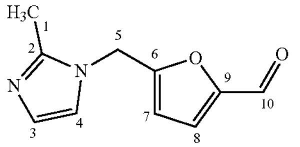

[Chem. I-NMR]

| No. | δ $^{1}H$ (ppm) | δ $^{13}C$ (ppm) |
|---|---|---|
| 1 | 2.42 | 13.5 |
| 2 | / | 144.7 |

TABLE 3-continued

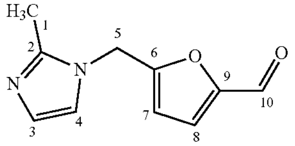

[Chem. I-NMR]

| No. | δ $^{1}H$ (ppm) | δ $^{13}C$ (ppm) |
|---|---|---|
| 3 | 7.18 | 127.3 |
| 4 | 6.85 | 119.7 |
| 5 | 5.28 | 46.4 |
| 6 | / | 153.3 |
| 7 | 6.55 | 111.8 |
| 8 | 7.35 | 122.1 |
| 9 | / | 152.9 |
| 10 | 9.59 | 177.5 |

Comparison of the Synthesis of 5-((2-Methyl-1H-Imidazol-1-Yl)Methyl)Furan-2-Carbaldehyde According to a Process in Accordance with the Invention (Example 1) and According to a Process not in Accordance with the Invention (Example 2)

Table 4 below demonstrates the advantages of the process for synthesizing the compound of formula (I) in accordance with the invention compared to a process not in accordance with the invention.

TABLE 4

| | Synthesis process in accordance with the invention (Example 1) | Synthesis process not in accordance with the invention (Example 2) |
|---|---|---|
| Yield of steps (iii) and (iv) | 46% | 14% |
| Molar purity | ≥90% | 80% |
| Appearance of the black deposit (humin) | FIG. 1(b) powdery appearance | FIG. 1(a) pasty appearance |
| Removal of humin from the reactor | Easy as it is friable | Difficult as it is tacky |

Example 3: Synthesis of 1-(5-((2-methyl-1H-imidazol-1-yl)methyl)furan-2-yl)-N-phenylmethanimine oxide (Compound of Formula (IIIa)) According to the Process in Accordance with the Invention The synthesis follows the Chem. SR2 reaction scheme below:

[Chem. SR2]

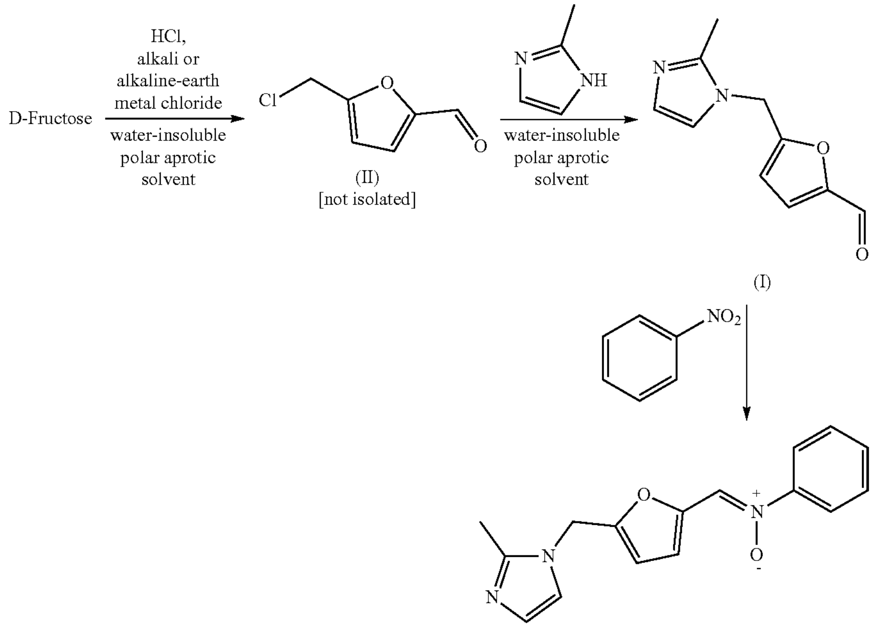

(II) [not isolated]

(I)

(IIIb)

The example below gives a preferred embodiment of the invention. Other embodiments are also possible.

D-fructose is purchased from Aldrich under the reference F0127.

Steps (i) to (iv) from Example 1 are carried out in an identical manner and the compound of formula (I) is obtained in a yield of 46% (60 g) and a molar purity of greater than 90%, determined by $^{1}H$ NMR in $CDCl_3$. The peaks of the $^{1}H$ and $^{13}C$ NMR spectra are detailed in Table 5 below with the numbering of the carbon atoms presented on the Chem. I-NMR formula.

TABLE 5

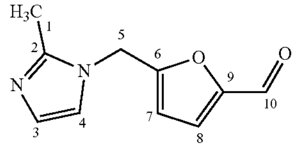

[Chem. I-NMR]

| No. | δ $^{1}H$ (ppm) | δ $^{13}C$ (ppm) |
|---|---|---|
| 1 | 2.42 | 13.5 |
| 2 | / | 144.7 |
| 3 | 7.18 | 127.3 |
| 4 | 6.85 | 119.7 |
| 5 | 5.28 | 46.4 |
| 6 | / | 153.3 |
| 7 | 6.55 | 111.8 |
| 8 | 7.35 | 122.1 |
| 9 | / | 152.9 |
| 10 | 9.59 | 177.5 |

Step (b). Condensation Reaction Between 5-((2-methyl-1H-imidazol-1-yl)methyl)furan-2-carbaldehyde (Compound of Formula (I)) and Phenylhydroxylamine to Obtain (5-((2-methyl-1H-imidazol-1-yl)methyl)furan-2-yl)-N-phenylmethanimine oxide (Compound of Formula (IIIa))

The compound of formula (I) (50 g, 1 equiv.) obtained in the preceding step is solubilized in ethanol (200 g) in a 500-ml reactor at ambient temperature (T=23° C.) in order to obtain a solution referred to as Sol. E. Ammonium chloride (15 g, i.e. 1.1 equiv. relative to the compound of formula (I)) is solubilized in a heel of water to obtain a solution referred to as Sol. F. The Sol. F solution is poured onto the Sol. E solution at room temperature and with stirring. Then nitrobenzene (32 g, 1 equiv. relative to the compound of formula (I)) is added to the reaction medium, with stirring, at room temperature. Stirring is carried out for 10 minutes at room temperature and the medium is then cooled to a temperature of 18° C. with stirring. Zinc (52 g, i.e. 3 equiv. relative to the compound of formula (I)) is then added in small portions in order to control the exothermicity of the reaction and to keep the temperature of the reaction medium at a temperature below or equal to 22° C. in order to limit parasitic chemistry. The reaction medium is stirred at 850 rpm for 4.5 hours.

The reaction is monitored by TLC (Rf(compound of formula (IIIa))=0.4-0.5), the elution solvent is a 90/10 (vol/vol) $CH_2Cl_2$/MeOH mixture. Visualization is carried out under a UV lamp at a wavelength of 254 nm or by NMR (disappearance of the aldehyde signal at 9.7 ppm).

Step (c): Recovery and Purification of 5-((2-methyl-1H-imidazol-1-yl)methyl)furan-2-yl)-N-phenylmethanimine Oxide (Compound of Formula (IIIa))

The solution obtained on conclusion of step (b) is filtered through a Buchner funnel (Sartorius™ filter of grade 391;

0.15 mm thick; retention of 2 to 3 μm particles) in order to eliminate the zinc. The solid, consisting mainly of zinc, is washed twice with ethanol (120 g), the mass of ethanol used for each wash corresponds to approximately 30% of the total mass of the reaction medium of step (b). The filtrates of orangey/yellow colour, which still contain a yellow/white precipitate, are combined. The combined filtrates are filtered a second time.

During filtration, a precipitate (zinc complexed with the compound of formula (IIIa)) and/or with the compound of formula (I) and reaction by-products) may form in the filtrate. This precipitate is soluble in dimethyl sulfoxide.

The volatile compounds are separated by introducing the filtrate into distillation equipment, such as a rotary evaporator, limiting the heating to avoid degradation of the compound of formula (IIIa) (boiler temperature <60° C., the distillation time is approximately 1 hour). The crude compound of formula (IIIa) is obtained in the form of a brown/orange solid. The yield of compound of formula (IIIa) obtained from the compound of formula (I) in this step is 80%, i.e. 80 g. The crude compound of formula (IIIa) is crystallized at 25° C. from an MTBE (methyl tert-butyl ether)/ethyl acetate mixture (67/33 vol/vol, i.e. 59 g MTBE and 29 g ethyl acetate respectively). The product obtained is separated in the form of a yellow precipitate from the MTBE/ethyl acetate mixture by filtration and the purity of the compound of formula (IIIa) obtained is measured by NMR.

The solid is finally dried for 1 hour under reduced pressure at 40° C. and then, at room temperature, under reduced pressure overnight. The yield of compound of formula (IIIa) obtained from the compound of formula (I) is 70% on conclusion of this step, i.e. 52 g, with a molar purity of greater than 90%. The peaks of the $^{1}H$ and $^{13}C$ NMR spectra are detailed in Table 6 below with the numbering of the carbon atoms presented on the Chem. IIIa-NMR formula.

TABLE 6

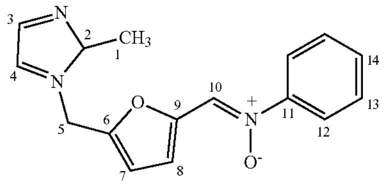

[Chem. IIIa-NMR]

| No. | δ $^{1}H$ (ppm) | δ $^{13}C$ (ppm) |
|---|---|---|
| 1 | 2.37 | 12.6 |
| 2 | / | 144.2 |
| 3 | 6.87 | 127.1 |
| 4 | 6.81 | 119 |
| 5 | 4.99 | 42.6 |
| 6 | / | 150.7 |
| 7 | 6.39 | 110.8 |
| 8 | 7.87 | 116.4 |
| 9 | / | 147.5 |
| 10 | 8.01 | 123.1 |
| 11 | / | 146.7 |
| 12 | 7.71 | 120.5 |
| 13 | 7.41 | 128.7 |
| 14 | 7.4 | 129.6 |

Example 4: Production of the Compound of Formula (IIIa) According to a Process not in Accordance with the Invention (5-Step Process with Isolation of the 4 Synthesis Intermediate Products)

1-(5-((2-Methyl-1H-imidazol-1-yl)methylfuran-2-yl)-N-phenylmethanimine oxide was obtained according to the Chem SR1 reaction scheme:

[Chem. SR1]

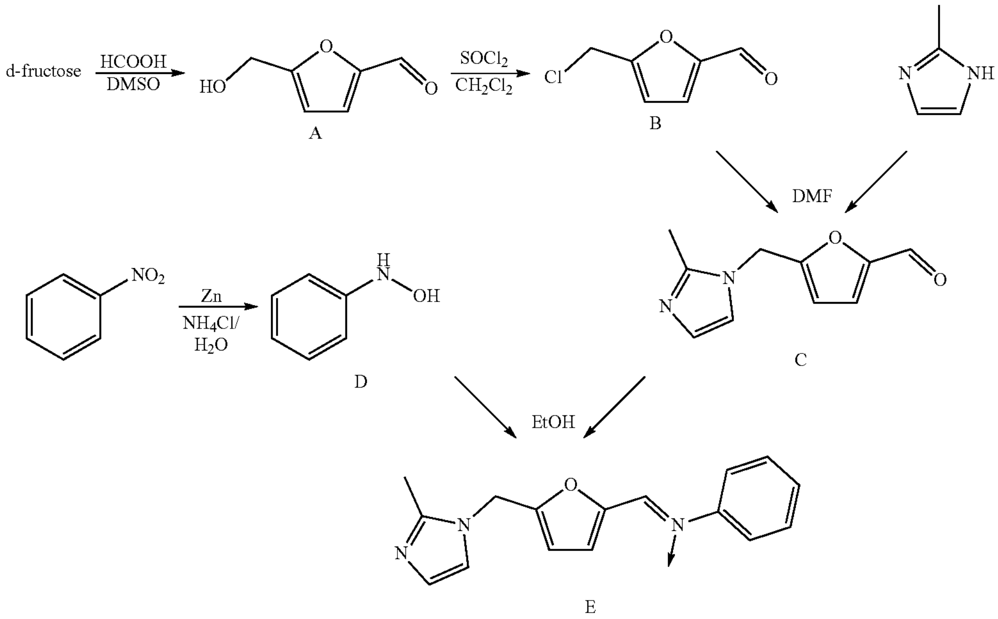

The step of converting fructose to 5-(hydroxymethyl) furan-2-carbaldehyde (compound A, CAS 67-47-0) in DMSO is described in Molecular Catalysis (2019), 465, 87-94, in paragraphs 2.4, 3.3 and scheme 2.

The step of converting 5-(hydroxymethyl)furan-2-carbaldehyde to 5-(chloromethyl)furan-2-carbaldehyde (compound B) was carried out on the basis of the article by Sanda, Komla et al., Synthesis of 5-(bromomethyl)- and of 5-(chloromethyl)-2-furancarboxaldehyde, Carbohydrate Research, 187(1), 15-23; 1989.

The synthesis of 5-((2-methyl-1H-imidazol-1-yl)methyl) furan-2-carbaldehyde (compound C) from 5-(chloromethyl) furan-2-carbaldehyde (compound B) is carried out in accordance with the protocol described in document WO 2020/249623 in paragraph 4.1, page 23.

The production of N-phenylhydroxylamine (compound D, CAS 100-65-2) from nitrobenzene is described in Organic Syntheses, Vol. 4. p. 57 (1925).

The synthesis of 1-(5-((2-methyl-1H-imidazol-1-yl) methyl)furan-2-yl)-N-phenylmethanimine oxide (compound E) is carried out in accordance with the protocol described in document WO 2020/249623 in paragraph 4.2, page 23.

In the end, a clear brown solid with a melting point of 147-150° C. is obtained with a yield, starting from the compound of formula C, of 68.4% (5.06 g; 17.99 mmol) and a molar purity of greater than 98% ($^1H$ NMR). The peaks of the $^1H$ and $^{13}C$ NMR spectra are detailed in Table 7 below with the numbering of the carbon atoms presented on the Chem. IIIa-NMR formula.

TABLE 7

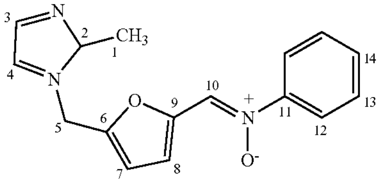

[Chem. IIIa-NMR]

| No. | δ $^1H$ (ppm) | δ $^{13}C$ (ppm) |
|---|---|---|
| 1 | 2.37 | 12.6 |
| 2 | / | 144.2 |
| 3 | 6.87 | 127.1 |
| 4 | 6.81 | 119 |
| 5 | 4.99 | 42.6 |
| 6 | / | 150.7 |
| 7 | 6.39 | 110.8 |
| 8 | 7.87 | 116.4 |
| 9 | / | 147.5 |
| 10 | 8.01 | 123.1 |
| 11 | / | 146.7 |
| 12 | 7.71 | 120.5 |
| 13 | 7.41 | 128.7 |
| 14 | 7.4 | 129.6 |

Example 5: Synthesis of the Compound of Formula (IIIa) According to a Process not in Accordance with the Invention (4-Step Process with Isolation of the 3 Intermediate Synthesis Products)

1-(5-((2-Methyl-1H-imidazol-1-yl)methylfuran-2-yl)-N-phenylmethanimine oxide was obtained according to the Chem SR3 reaction scheme below:

[Chem. SR3]

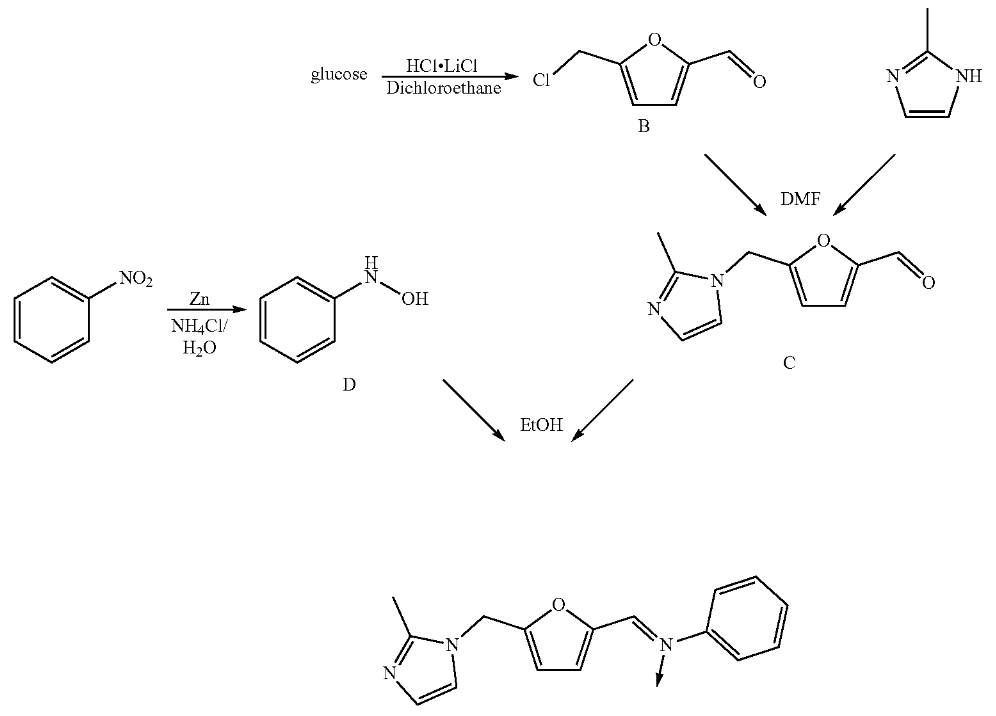

The synthesis of 5-(chloromethyl)furan-2-carbaldehyde (compound B) from glucose without isolating compound A is derived from the article in Angew. Chem, Int. Ed., 2008, 47, 7924-7926 and more precisely the last paragraph on page 7924 and the first paragraph on page 7925.

The synthesis of 5-((2-methyl-1H-imidazol-1-yl)methyl) furan-2-carbaldehyde (compound C) from 5-(chloromethyl) furan-2-carbaldehyde (compound B) is carried out in accordance with the protocol described in document WO 2020/249623 in paragraph 4.1, page 23.

The production of N-phenylhydroxylamine (compound D, CAS 100-65-2) from nitrobenzene is described in Organic Syntheses, Vol. 4. p. 57 (1925).

The synthesis of 1-(5-((2-methyl-1H-imidazol-1-yl) methyl)furan-2-yl)-N-phenylmethanimine oxide (compound E) is carried out in accordance with the protocol described in document WO 2020/249623 in paragraph 4.2, page 23.

In the end, a clear brown solid with a melting point of 147-150° C. is obtained with a yield, starting from the compound of formula C, of 68.4% (5.06 g; 17.99 mmol) and a molar purity of greater than 98% ($^1$H NMR). The peaks of the $^1$H and $^{13}$C NMR spectra are detailed in Table 8 below with the numbering of the carbon atoms presented on the Chem. IIIa-NMR formula.

TABLE 8

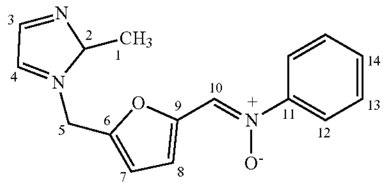

[Chem. IIIa-NMR]

| No. | δ $^1$H (ppm) | δ $^{13}$C (ppm) |
|---|---|---|
| 1 | 2.37 | 12.6 |
| 2 | / | 144.2 |
| 3 | 6.87 | 127.1 |
| 4 | 6.81 | 119 |
| 5 | 4.99 | 42.6 |
| 6 | / | 150.7 |
| 7 | 6.39 | 110.8 |
| 8 | 7.87 | 116.4 |
| 9 | / | 147.5 |
| 10 | 8.01 | 123.1 |
| 11 | / | 146.7 |
| 12 | 7.71 | 120.5 |
| 13 | 7.41 | 128.7 |
| 14 | 7.4 | 129.6 |

Comparison Between the Synthesis Process in Accordance with the Invention (Example 3) and the Synthesis Processes not in Accordance with the Invention (Examples 4 and 5) (Taking into Account the Solvents and the Water Introduced, without the Reactants)

Table 9 below compares the number of steps, the number of intermediate synthesis products which have been isolated, the overall yield of the process and the nature of the solvent as well as their quantity for each example.

For Example 3, the solvents, the amounts of solvent and the yields indicated in Table 9 are obtained from the experimental data above.

For Examples 4 and 5, the solvents, the amounts of solvent and the yields indicated in Table 9 are obtained from the literature and paragraphs 4.1 and 4.2 on page 23 of document WO 2020/249623.

More specifically, for Example 4, the data (type of solvent, amount, yield) for the synthesis of 5-(hydroxymethyl) furan-2-carbaldehyde (compound A) from fructose in DMSO is obtained from the article in Molecular Catalysis (2019), 465, 87-94. Paragraphs 2.4, 3.3 and scheme 2 from this reference indicate that an oxo-rhenium complex $HReO_4$ (0.025 g, 10 mol %) is added to a Schlenk flask equipped with a J. Young tap, the flask containing a solution of fructose (0.180 g, 1.0 mmol of fructose) in DMSO (5 ml). The reaction mixture is stirred for one hour at 140° C. in the sealed Schlenk flask. Compound A is obtained with a reaction yield equal to 100%. The synthesis of 5-(chloromethyl)furan-2-carbaldehyde (compound B) from compound A for Example 4 was carried out on the basis of the article in Carbohydrate Research, 187(1), 15-23; 1989. More specifically, $SOCl_2$ (20 ml, 276 mmol) is added dropwise at −5° C. to a solution of 29 g of 5-(hydroxymethyl)furan-2-carbaldehyde (230 mmol) in dichloromethane (120 ml) over 35 min. Once the addition is complete, the reaction medium is heated gradually to 10° C. for 50 min. The solution is finally concentrated under reduced pressure to yield an oil (34.2 g). An ethyl acetate/petroleum ether (40/60) mixture is added to the crude product to obtain a solution with a precipitate. The solution is filtered on a silica gel/activated carbon mixture and then washed with the ethyl acetate/petroleum ether (40/60) mixture. The filtrate is finally concentrated under reduced pressure (3 mbar, 32° C.) to give compound B with a yield of 54% (18 g).

For Example 5, the data (type of solvent, amount, yield) for the synthesis of 5-(chloromethyl)furan-2-carbaldehyde (compound B) from glucose without isolating compound A is derived from the article in Angew. Chem, Int. Ed., 2008, 47, 7924-7926 and more specifically the last paragraph on page 7924 and the first paragraph on page 7925.

For Examples 4 and 5, the data (type of solvent, amount, yield) concerning the synthesis of 5-((2-methyl-1H-imidazol-1-yl)methyl)furan-2-carbaldehyde (product C) from product B and 2-methylimidazole is derived from paragraph 4.1, page 23 of document WO 2020/249623. More specifically, a mixture of 2-methylimidazole (4.83 g; 58.80 mmol; 2.5 eq.) and 5-(chloromethyl)furan-2-carbaldehyde (3.40 g; 23.52 mmol) in DMF (4 ml) is heated to a bath temperature of 70° C. After stirring for 2-3 hours at this temperature and 2 hours at a bath temperature of 80° C., the reaction medium is diluted with water (50 ml) and the organic phase is then separated out. The aqueous phase is extracted four times with dichloromethane (4×20 ml). The organic phase fractions are combined and then washed with water (4×5 ml) and then concentrated under reduced pressure (2-3 mbar; 32° C.) to give a black oil (2.44 g; 12.8 mmol) in a yield of 55%. This product is used in the following step without further purification.

For Examples 4 and 5, the data (type of solvent, amount, yield) for the synthesis of phenylhydroxylamine (product D) from nitrobenzene is derived from Organic Syntheses; Vol. 4. p. 57 (1925). The product N-phenylhydroxylamine (compound D, CAS 100-65-2) is synthesized from nitrobenzene according to the procedure described in Vol. 4. p. 57 (1925). More specifically, in a 500 ml reaction flask fitted with a mechanical stirrer, 5 g of ammonium chloride are dissolved in 160 ml of water. 10 g of nitrobenzene are added to this solution. The reaction flask is cooled with chilled water and, over one hour, gradually in small portions, with good stirring, 15 g of zinc powder are added while maintaining the temperature constantly between 14° C. and 16° C. Once the addition of the zinc powder has been completed, the mixture is left to stand at room temperature with constant stirring for a further 10 minutes. The reaction solution is filtered in order to separate it from the zinc oxide. The first filtrate is recovered and separated by pouring it into a beaker. The zinc oxide in the funnel collected by filtration is carefully washed with 200 ml of water at 40° C. and the second filtrate is separated by pouring it into a second beaker. The two filtered solutions are cooled separately in chilled water and are saturated with finely pulverized sodium chloride, with stirring. The amount of sodium chloride for the first solution is about 45 g and for the second solution is about 60 g. The deposited colourless crystals of crude phenylhydroxylamine are filtered off and, without washing, are dried under vacuum. The crude phenylhydroxylamine is purified by crystallization from a product giving benzene, which melts at 81° C.

For Examples 4 and 5, the data (type of solvent, amount, yield) for the synthesis of 1-5-((2-methyl-1H-imidazol-1-yl)methyl)furan-2-yl)-N-phenylmethanimine oxide (product E) from product D is derived from paragraph 4.2, page 23 of document WO 2020/249623. More specifically, N-phenylhydroxylamine (compound of formula (D) previously obtained; 2.87 g; 26.3 mmol; 1 eq.) is added portionwise over 5 minutes to a solution of 5-((2-methyl-1H-imidazol-1-yl)methyl)furan-2-carbaldehyde (compound of formula (C) previously obtained (5.00 g; 26.3 mmol) in ethanol (5 ml) at a bath temperature of 35-40° C. The reaction medium is heated up to a bath temperature of 60° C. After stirring for 1.5 hours at this temperature and then returning to a temperature of 30-35° C., tert-butyl methyl ether (15 ml) is added dropwise. After stirring for one hour at room temperature (23° C.), the precipitate obtained is filtered off and washed on the filter with a mixture of ethanol and tert-butyl methyl ether (1 ml and 5 ml) and then with tert-butyl methyl ether (8 ml). A clear brown solid with a melting point of 147-150° C. is obtained with a yield of 68.4% (5.06 g; 17.99 mmol) and a molar purity of greater than 9800 ($^1$H NMR).

TABLE 9

| | Synthesis process in accordance with the invention (Example 3) | Synthesis process not in accordance with the invention (Example 4) | Synthesis process not in accordance with the invention (Example 5) |
|---|---|---|---|
| Number of chemical steps | 2 | 5 | 4 |
| Isolation of synthetic intermediate products | 1 | 4 | 3 |
| Overall yield obtained over the entire process | 25% | 16% | 26% |
| Solvent | | per 1 kg of end product (in kg) | |
| DMSO | 0.0 | 123.3 | 0.0 |
| Toluene | 90.0 | 0.7 | 0.7 |
| Dichloromethane | 0.0 | 66.0 | 277.0 |
| Dichloroethane | 0.0 | 0.0 | 1200.0 |
| DMF | 0.0 | 1.5 | 1.5 |
| Ethanol | 2.1 | 1.0 | 1.0 |
| Methanol | 0.0 | 0.0 | 6.0 |
| MTBE | 0.0 | 3.0 | 3.0 |
| Diethyl ether | 0.0 | 0.0 | 60.0 |
| Petroleum ether | 0.0 | 4.5 | 0.0 |
| Total organic solvent | 92.1 | 200 | 1549.2 |
| Water | 14.4 | 33.8 | 33.8 |

As can be seen in Table 9, the process according to the invention (Example 3) requires fewer different organic solvents (2 versus 6) and a lower total amount of organic solvents than the pathway of Example 4 (92.1 kg versus 200 kg). The pathway according to the invention is also intended to be more productive: the concentration of the species is higher, the reaction times are reduced, the yield is improved. The total yield is also improved.

The pathway of Example 5, compared to the synthesis process of the invention, makes it possible to obtain the product of formula (IIIa) with the same overall reaction yield. However, in this Example 5, not in accordance with the invention, toxic organic solvents are used (e.g. dichloroethane) in large quantities which are difficult to viable on an industrial scale. Moreover, the number of different organic solvents is higher (7 versus 2) than for the synthesis process according to the invention, as is the total amount of organic solvents (1549.2 kg versus 200 kg).

Example 6: Synthesis of the Compound of Formula (IIIb) According to a Process in Accordance with the Invention The compound of formula (IIIb) is synthesized according to the Chem. SR4 reaction scheme below:

[Chem. SR4]

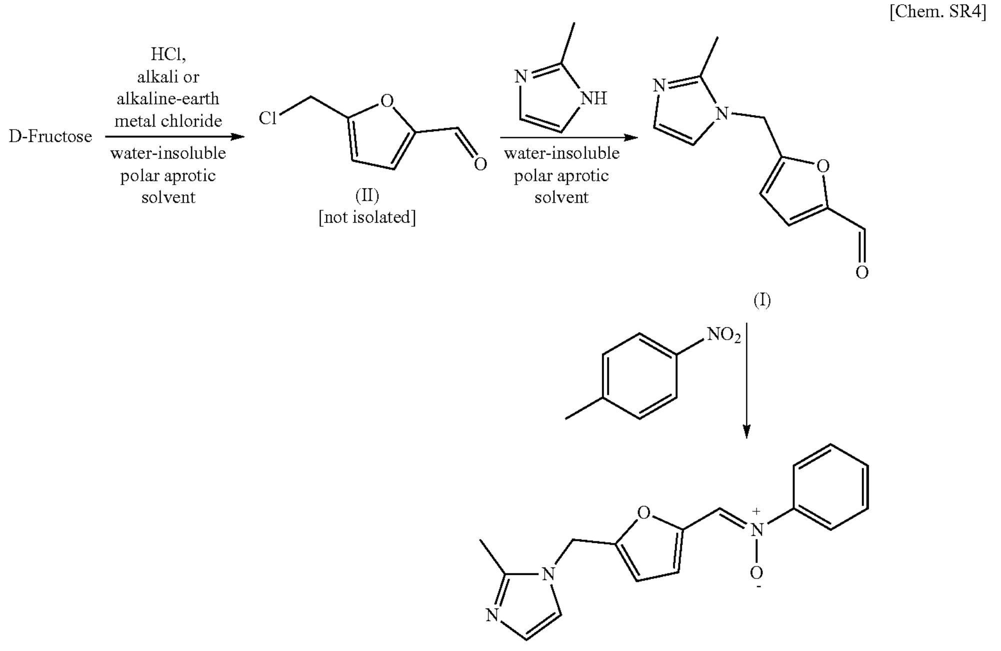

(IIIb)

Step (a): Synthesis of 5-((2-methyl-1H-imidazol-1-yl)methyl)furan-2-carbaldehyde (Compound of Formula I)

The compound of formula (I) is synthesized according to steps (i) to (iv) of the process according to the invention starting from D-fructose (see Example 1).

Step (b): Condensation Reaction Between 5-((2-methyl-1H-imidazol-1-yl)methyl)furan-2-carbaldehyde (Compound of Formula (I)) and N-(p-tolyl) hydroxylamine to Obtain 5-((2-methyl-1H-imidazol-1-yl)methyl)furan-2-yl)-N-tolylmethanimine Oxide (Compound of Formula (IIIb))

The compound of formula (I) (50 g, 1 equiv.) obtained in the preceding step is solubilized in ethanol (200 g) in a 500-ml reactor at ambient temperature (T=23° C.) in order to obtain a solution referred to as Sol. E. Ammonium chloride (15 g, i.e. 1.1 equiv. relative to the compound of formula (I)) is solubilized in a heel of water to obtain a solution referred to as Sol. F. The Sol. F solution is poured onto the Sol. E solution at room temperature and with stirring. Then 4-nitrotoluene (36 g, 1 equiv. relative to the compound of formula (I)) is added to the reaction medium, with stirring, at room temperature. Stirring is carried out for 10 minutes at room temperature and the medium is then cooled to a temperature of 18° C. with stirring. Zinc (52 g, i.e. 3 equiv. relative to the compound of formula (I)) is then added in small portions in order to control the exothermicity of the reaction and to keep the temperature of the reaction medium at a temperature below or equal to 22° C. in order to limit parasitic chemistry. The reaction medium is stirred at 850 rpm for 4.5 hours.

The reaction is monitored by TLC (Rf(compound of formula (IIIb))=0.4-0.5), the elution solvent is a 90/10 (vol/vol) $CH_2Cl_2$/MeOH mixture. Visualization is carried out under a UV lamp at a wavelength of 254 nm or by NMR (disappearance of the aldehyde signal at 9.7 ppm).

Step (c): Recovery and Purification of (5-((2-methyl-1H-imidazol-1-yl)methyl)furan-2-yl)-N-tolylmethanimine Oxide (Compound of Formula (IIIb))

The solution obtained on conclusion of step (b) is filtered through a Buchner funnel (Sartorius™ filter of grade 391; 0.15 mm thick; retention of 2 to 3 μm particles) in order to eliminate the zinc. The solid, consisting mainly of zinc, is washed twice with ethanol (120 g for each wash). The filtrates of orangey/yellow colour, which still contain a yellow/white precipitate, are combined. The combined filtrates are filtered a second time.

During filtration, a precipitate (zinc complexed with the compound of formula (IIIb)) and/or with the compound of formula (I) and reaction by-products) may form in the filtrate. This precipitate is soluble in dimethyl sulfoxide.

The volatile compounds are separated by introducing the filtrate into distillation equipment, such as a rotary evaporator, limiting the heating to avoid degradation of the compound of formula (IIIb) (boiler temperature <60° C., the distillation time is approximately 1 hour). The crude compound of formula (IIIb) is obtained in the form of a brown/orange solid. The yield of compound of formula (IIIb) obtained from the compound of formula (I) in this step is 80%, i.e. 80 g. The crude compound of formula (IIIb) is crystallized at 25° C. from an MTBE (methyl tert-butyl ether)/ethyl acetate mixture (67/33 vol/vol, i.e. 59 g MTBE and 29 g ethyl acetate respectively). The product obtained is separated in the form of a yellow precipitate from the MTBE/ethyl acetate mixture by filtration and the purity of the compound of formula (IIIb) obtained is measured by NMR.

The solid is finally dried for 1 hour under reduced pressure at 40° C. and then, at room temperature, under reduced pressure overnight. The yield of compound of formula (IIIb) obtained from the compound of formula (I) is 65% on conclusion of this step, i.e. 50 g, with a molar purity of greater than 90%. The peaks of the $^{1}H$ and $^{13}C$ NMR spectra are detailed in Table 10 below with the numbering of the carbon atoms presented on the Chem. IIIb-NMR formula.

TABLE 10

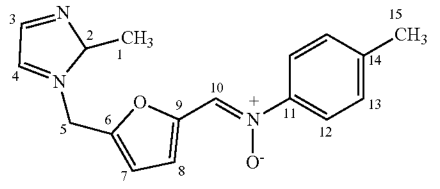

[Chem. IIIb-NMR]

| No. | δ $^{1}H$ (ppm) | δ $^{13}C$ (ppm) |
|---|---|---|
| 1 | 2.37 | 21.3 |
| 2 | / | 144.7 |
| 3 | 6.9 | 127.2 |
| 4 | 6.8 | 119.2 |
| 5 | 4.99 | 43.4 |
| 6 | / | 151.4 |
| 7 | 6.8 | 110.8 |
| 8 | 7.8 | 116.6 |
| 9 | / | 148.1 |
| 10 | 7.99 | 123.2 |
| 11 | / | 147.2 |
| 12 | 7.6 | 117.7 |
| 13 | 7.2 | 129.6 |
| 14 | / | 141.5 |
| 15 | 2.4 | 13.4 |

The invention claimed is:

1. A method for the preparation of a compound of formula I:

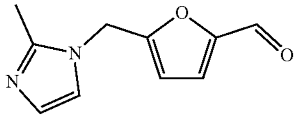

comprising the following successive steps:

(i) preparing a mixture comprising a carbohydrate, an alkali or alkaline-earth metal chloride, hydrochloric acid, water, and an organic solvent, the mixture being heated to a temperature within a range of from 35° C. to 90° C., the organic solvent being a water-insoluble polar aprotic solvent, and the carbohydrate being a monosaccharide, a polysaccharide or a mixture thereof;

(ii) cooling the mixture obtained from step (i) to give a cooled mixture, separating the cooled mixture into an aqueous phase and an organic phase, and recovering the organic phase, the organic phase comprising the organic solvent and a compound of formula II:

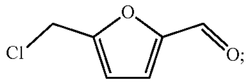

(iii) mixing 2-methylimidazole and the organic phase obtained from step (ii), the 2-methylimidazole being in molar excess relative to the compound of formula II; and (iv) recovering the compound of formula I formed following step (iii).

2. The method according to claim 1, wherein the carbohydrate is a monosaccharide.

3. The method according to claim 1, wherein the organic solvent is toluene.

4. The method according to claim 1, wherein, during step (i), an amount of hydrochloric acid is within a range of from 3 to 7 molar equivalents relative to an amount of monosaccharide units present in the carbohydrate.

5. The method according to claim 1, wherein, during step (i), an amount of chloride ions supplied by the alkali or alkaline-earth metal chloride is within a range of from 1.2 to 2.6 molar equivalents relative to an amount of monosaccharide units present in the carbohydrate.

6. The method according to claim 1, wherein the alkali or alkaline-earth metal chloride is selected from the group consisting of magnesium chloride and lithium chloride.

7. The method according to claim 1, wherein the phase-transfer agent is a quaternary ammonium halide, an amount of which is within a range of from 0.001 to 0.01 molar equivalents relative to an amount of monosaccharide units present in the carbohydrate.

8. The method according to claim 1, wherein step (i) comprises the following steps:

(i1) preparing a composition comprising the carbohydrate, the alkali or alkaline-earth metal chloride, the hydrochloric acid, and the water; and (i2) adding the composition obtained from step (i1) to the organic solvent heated to a temperature within a range of from 35° C. to 90° C.; or (i1) adding the carbohydrate to the organic solvent heated to a temperature within a range of from 35° C. to 90° C.;

(i2) preparing a composition comprising the alkali or alkaline-earth metal chloride, the hydrochloric acid, and the water; and (i3) adding the composition obtained from step (i2) to the heated organic solvent comprising the carbohydrate obtained from step (i1); or (i1) preparing a composition comprising the carbohydrate and the water;

(i2) preparing a composition comprising the organic solvent, the hydrochloric acid, and the alkali or alkaline-earth metal chloride, the composition being heated to a temperature within a range of from 35°° C. to 90° C.; and (i3) adding the composition obtained from step (i1) to the heated composition obtained from step (i2); or (i1) preparing a composition comprising the organic solvent, the hydrochloric acid, the alkali or alkaline-earth metal chloride, and the water, the composition being heated to a temperature within a range of from 35° C. to 90° C.; and (i2) adding the carbohydrate to the heated composition obtained from step (i1); or (i1) preparing a composition comprising the carbohydrate, the organic solvent, and the alkali or alkaline-earth metal chloride, the composition being heated to a temperature within a range of from 35° C. to 90° C.; and (i2) adding a solution of hydrochloric acid to the heated composition obtained from step (i1).

9. The method according to claim 1, wherein step (ii) comprises, after the cooling step and before the separation step, a step of filtering the cooled mixture in order to remove solid materials present.

10. The method according to claim 1, wherein an amount of 2-methylimidazole during step (iii) is within a range of from 2.0 to 3.0 molar equivalents relative to an amount of the compound of formula II.

11. The method according to claim 1, wherein the mixture obtained during step (iii) comprising the 2-methylimidazole and the organic phase obtained from step (ii) is maintained at a temperature within a range of from 50° C. to 90° C. for a period of time within a range of from 2 to 8 hours.

12. The method according to claim 1, wherein step (iii) comprises the following steps:

(iii1) adding, at room temperature, a fraction of the organic phase obtained from step (ii) to the 2-methylimidazole;

(iii2) heating the composition obtained from step (iii1) to a temperature within a range of from 50° C. to 90° C.; and (iii3) adding a remaining fraction of the organic phase obtained from step (ii) to the heated composition obtained from step (iii2); or (iii1) adding the 2-methylimidazole to the organic phase obtained from step (ii) heated to a temperature within a range of from 50° C. to 90° C.

13. A method for the preparation of a compound of formula III:

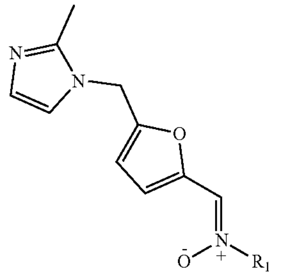

comprising the following steps:

(a) preparing a compound of formula I by the process according to claim 1;

(b) reacting the compound of formula I obtained in step (a) with a compound of formula $R_1$-$NO_2$ in a presence of a reducing agent, in order to form the compound of formula III; and (c) recovering the compound of formula III, wherein $R_1$ is selected from the group consisting of linear or branched $C_1$-$C_{20}$ alkyls, $C_3$-$C_{20}$ cycloalkyls not substituted or substituted with one or more linear or branched aliphatic hydrocarbon chains, and $C_6$-$C_{20}$ aryls not substituted or substituted with one or more linear or branched aliphatic hydrocarbon chains.

14. The method according to claim 13, wherein step (b) comprises the following steps:

(b1) preparing a composition comprising the compound of formula I obtained in step (a), an ammonium salt and a water/ethanol mixture;

(b2) adding the compound $R_1$-$NO_2$ to the composition obtained in step (b1); and (b3) adding zinc as the reducing agent to the composition obtained in step (b2) maintained at a temperature in a range of from 15° C. to 25° C. during the addition step.

15. The method according to claim 14, wherein the composition resulting from step (b3) is maintained at a temperature in a range of from 15° C. to 25° C. for a period of time within a range of from 4 to 6 hours.

16. The method according to claim 1, wherein, in step (i), the mixture further comprises a phase-transfer agent.

17. The method according to claim 1, wherein, in step (i), the mixture is heated to a temperature within a range of from 55° to 75°.

18. The method according to claim 1, wherein the carbohydrate is fructose.

19. The method according to claim 16, wherein step (i) comprises the following steps:

(i1) preparing a composition comprising the carbohydrate, the alkali or alkaline-earth metal chloride, the hydrochloric acid, the water, and the phase-transfer agent; and (i2) adding in semi-continuous mode the composition obtained from step (i1) to the organic solvent heated to a temperature within a range of from 55° C. to 75° C.; or (i1) adding the carbohydrate to the organic solvent heated to a temperature within a range of from 55° C. to 75° C.;

(i2) preparing a composition comprising the alkali or alkaline-earth metal chloride, the hydrochloric acid, the water, and the phase-transfer agent; and (i3) adding in semi-continuous mode the composition obtained from step (i2) to the heated organic solvent comprising the carbohydrate obtained from step (i1); or (i1) preparing a composition comprising the carbohydrate and the water;

(i2) preparing a composition comprising the organic solvent, the hydrochloric acid, the alkali or alkaline-earth metal chloride, and the phase-transfer agent, the composition being heated to a temperature within a range of from 55° C. to 75° C.; and (i3) adding in semi-continuous mode, the composition obtained from step (i1) to the heated composition obtained from step (i2); or (i1) preparing a composition comprising the organic solvent, the hydrochloric acid, the alkali or alkaline-earth metal chloride, the water and the phase-transfer agent, the composition being heated to a temperature within a range of from 55° C. to 75° C.; and (i2) adding the carbohydrate to the heated composition obtained from step (i1); or (i1) preparing a composition comprising the carbohydrate, the organic solvent, the alkali or alkaline-earth metal chloride, and the phase-transfer agent, the composition being heated to a temperature within a range of from 55° C. to 75° C.; and (i2) adding in semi-continuous mode, a solution of hydrochloric acid to the heated composition obtained from step (i1).

* * * * *